US008802087B2

(12) United States Patent
Shlieout et al.

(10) Patent No.: US 8,802,087 B2
(45) Date of Patent: Aug. 12, 2014

(54) PHARMACEUTICAL COMPOSITIONS OF LIPASE-CONTAINING PRODUCTS, IN PARTICULAR OF PANCREATION

(75) Inventors: George Shlieout, Sehnde (DE); Bernd Boedecker, Hannover (DE); Siegfried Schaefer, Burgwedel/Thoense (DE); Bernd Thumbeck, Nordstemmen (DE); Peter-Colin Gregory, Hannover (DE)

(73) Assignee: Abbott Products GmbH, Hanover (DE)

( * ) Notice: Subject to any disclaimer, the term of this patent is extended or adjusted under 35 U.S.C. 154(b) by 0 days.

(21) Appl. No.: 11/085,073

(22) Filed: Mar. 22, 2005

(65) Prior Publication Data

US 2005/0250817 A1 Nov. 10, 2005

Related U.S. Application Data

(60) Provisional application No. 60/554,993, filed on Mar. 22, 2004.

(30) Foreign Application Priority Data

Mar. 22, 2004 (EP) .................................... 04101164

(51) Int. Cl.
| | |
|---|---|
| *A61K 38/46* | (2006.01) |
| *A61K 31/745* | (2006.01) |
| *A61K 38/48* | (2006.01) |
| *A61K 9/107* | (2006.01) |
| *A61K 38/47* | (2006.01) |
| *A61K 9/16* | (2006.01) |
| *A61K 31/22* | (2006.01) |

(52) U.S. Cl.
CPC ............... *A61K 31/745* (2013.01); *A61K 38/48* (2013.01); *A61K 9/1075* (2013.01); *A61K 38/47* (2013.01); *A61K 9/1641* (2013.01); *A61K 38/465* (2013.01); *A61K 31/22* (2013.01); *A61K 9/1617* (2013.01)
USPC ........ 424/94.6; 424/94.3; 424/94.2; 424/400; 424/94.29

(58) Field of Classification Search
CPC ............................... A61K 38/46; A61K 31/44
USPC ........................................................ 424/94.6
See application file for complete search history.

(56) References Cited

U.S. PATENT DOCUMENTS

| | | | |
|---|---|---|---|
| 3,324,002 A | 6/1967 | Antonides |
| 3,803,305 A | 4/1974 | Thuillier |
| 3,950,508 A | 4/1976 | Mony et al. |
| 3,956,483 A | 5/1976 | Lewis |
| 3,986,927 A | 10/1976 | Melnick et al. |
| 3,991,180 A | 11/1976 | Boettner et al. |
| 4,019,958 A | 4/1977 | Hell et al. |
| 4,079,125 A | 3/1978 | Sipos |
| 4,106,991 A | 8/1978 | Markussen et al. |
| 4,242,219 A | 12/1980 | Bogerman et al. |
| 4,280,971 A | 7/1981 | Wischniewski et al. |
| 4,447,412 A | 5/1984 | Bilton |
| 4,490,361 A | 12/1984 | Heldebrant |
| 4,533,562 A | 8/1985 | Ikegami et al. |
| 4,623,624 A | 11/1986 | Schultze |
| 4,689,297 A | 8/1987 | Good et al. |
| 4,775,536 A | 10/1988 | Patell |
| 4,786,505 A | 11/1988 | Lovgren et al. |
| 4,929,774 A | 5/1990 | Fukamachi et al. |
| 5,068,110 A | 11/1991 | Fawzi et al. |
| 5,219,572 A | 6/1993 | Sivaramakrishnan et al. |
| 5,225,202 A | 7/1993 | Hodges et al. |
| 5,260,074 A | 11/1993 | Sipos |
| 5,300,433 A | 4/1994 | Hrinda et al. |
| 5,302,400 A | 4/1994 | Sipos |
| 5,324,649 A | 6/1994 | Arnold et al. |
| 5,374,657 A | 12/1994 | Kyle |
| 5,378,462 A | 1/1995 | Boedecker et al. |
| 5,489,530 A | 2/1996 | Braatz et al. |
| 5,536,661 A | 7/1996 | Boel et al. |
| 5,570,104 A | 10/1996 | Hayashi |
| 5,614,189 A | 3/1997 | Huge-Jensen |
| 5,618,710 A | 4/1997 | Navia et al. |
| 5,645,832 A | 7/1997 | Braatz et al. |
| 5,658,871 A | 8/1997 | Batenburg et al. |

(Continued)

FOREIGN PATENT DOCUMENTS

| | | |
|---|---|---|
| CA | 2263703 A1 | 8/1999 |
| DE | 2035739 A1 | 1/1972 |

(Continued)

OTHER PUBLICATIONS

International Search Report dated Jun. 24, 2005.

(Continued)

*Primary Examiner* — Jon P Weber
*Assistant Examiner* — Tiffany Gough
(74) *Attorney, Agent, or Firm* — Lisa V. Mueller; Michael Best & Friedrich LLP

(57) ABSTRACT

Orally administrable pharmaceutical compositions of lipase-containing products, particularly pancreatin and pancreatin-containing products, or of enzyme products which contain at least one lipase of non-animal, especially microbial origin, which improve the lipolytic activity and particularly result in stabilization of the lipase in the acidic pH range. These oral pharmaceutical compositions contain a system which includes at least one surfactant and one co-surfactant and optionally a lipophilic phase, and are self-emulsifiable on contact with a hydrophilic and a lipophilic phase. The compositions according to the invention are suitable for treating or inhibiting maldigestion, especially maldigestion due to chronic exocrine pancreatic insufficiency, in mammals and humans.

43 Claims, No Drawings

(56) References Cited

U.S. PATENT DOCUMENTS

| | | | |
|---|---|---|---|
| 5,719,115 A | 2/1998 | Paatz et al. | |
| 5,750,104 A | 5/1998 | Sipos | |
| 5,750,148 A | 5/1998 | Maruyama et al. | |
| 5,766,912 A | 6/1998 | Boel et al. | |
| 5,783,545 A | 7/1998 | Paatz et al. | |
| 5,801,022 A | 9/1998 | Navia et al. | |
| 5,849,296 A | 12/1998 | Navia et al. | |
| 5,863,759 A | 1/1999 | Boel et al. | |
| 5,869,438 A | 2/1999 | Svendsen et al. | |
| 5,874,558 A | 2/1999 | Boel et al. | |
| 5,879,920 A | 3/1999 | Dale et al. | |
| 5,976,529 A | 11/1999 | Navia et al. | |
| 5,993,806 A | 11/1999 | Galle | |
| 6,004,768 A | 12/1999 | Navia et al. | |
| 6,011,001 A | 1/2000 | Navia et al. | |
| 6,025,391 A | 2/2000 | Haeberlin et al. | |
| 6,030,798 A | 2/2000 | Braatz et al. | |
| 6,051,220 A | 4/2000 | Scharpe | |
| 6,054,136 A | 4/2000 | Farah et al. | |
| 6,140,475 A | 10/2000 | Margolin et al. | |
| 6,187,572 B1 | 2/2001 | Platz et al. | |
| 6,224,910 B1 | 5/2001 | Ullah et al. | |
| 6,267,985 B1* | 7/2001 | Chen et al. | 424/451 |
| 6,278,794 B1 | 8/2001 | Parekh et al. | |
| 6,312,704 B1 | 11/2001 | Farah et al. | |
| 6,348,442 B2 | 2/2002 | Markussen | |
| 6,355,461 B2 | 3/2002 | Henriksen et al. | |
| 6,426,091 B1 | 7/2002 | Okumura et al. | |
| 6,692,771 B2* | 2/2004 | Pather et al. | 424/498 |
| 6,734,188 B1 | 5/2004 | Rhodes et al. | |
| 6,749,851 B2 | 6/2004 | Mann et al. | |
| 6,767,729 B1 | 7/2004 | Nagano et al. | |
| 7,211,281 B2 | 5/2007 | Van Beek et al. | |
| 7,479,378 B2 | 1/2009 | Potthoff et al. | |
| 2001/0046493 A1 | 11/2001 | Margolin et al. | |
| 2002/0061302 A1 | 5/2002 | Sander-Struckmeier et al. | |
| 2002/0137156 A1 | 9/2002 | Margolin et al. | |
| 2002/0146451 A1 | 10/2002 | Sharma et al. | |
| 2003/0007962 A1 | 1/2003 | Vergez et al. | |
| 2003/0017144 A1 | 1/2003 | Margolin et al. | |
| 2003/0021844 A1 | 1/2003 | Barthelemy et al. | |
| 2003/0049245 A1 | 3/2003 | Mann et al. | |
| 2003/0086948 A1* | 5/2003 | Benameur et al. | 424/400 |
| 2003/0104048 A1* | 6/2003 | Patel et al. | 424/451 |
| 2003/0175259 A1 | 9/2003 | Karageozian et al. | |
| 2003/0180352 A1 | 9/2003 | Patel et al. | |
| 2003/0211127 A1 | 11/2003 | Margolin et al. | |
| 2004/0013697 A1 | 1/2004 | Berndt et al. | |
| 2004/0033220 A1 | 2/2004 | Hartmann | |
| 2004/0057944 A1 | 3/2004 | Galle et al. | |
| 2004/0101562 A1 | 5/2004 | Maio | |
| 2004/0161423 A1 | 8/2004 | Kumar | |
| 2004/0202643 A1 | 10/2004 | Margolin et al. | |
| 2004/0213847 A1 | 10/2004 | Matharu et al. | |
| 2007/0148151 A1 | 6/2007 | Frink | |
| 2007/0148152 A1 | 6/2007 | Shlieout et al. | |
| 2007/0148153 A1 | 6/2007 | Shlieout | |
| 2008/0019959 A1 | 1/2008 | Becher et al. | |
| 2008/0292610 A1 | 11/2008 | Hartmann | |
| 2009/0130063 A1 | 5/2009 | Becher et al. | |
| 2009/0226414 A1 | 9/2009 | Tijssen et al. | |

FOREIGN PATENT DOCUMENTS

| | | |
|---|---|---|
| DE | 2410241 A1 | 9/1975 |
| DE | 25 12 746 A | 9/1976 |
| DE | 2626109 A1 | 12/1976 |
| DE | 2923279 C2 | 11/1980 |
| DE | 36 42 853 A1 | 6/1988 |
| DE | 42 03 315 A1 | 8/1992 |
| DE | 4200002 | 7/1993 |
| DE | 4322229 A1 | 1/1995 |
| DE | 4344215 A1 | 6/1995 |
| DE | 19907764 A1 | 11/1999 |
| DE | 19848849 A1 | 4/2000 |
| DE | 19856415 | 6/2000 |
| DE | 10012095 A1 | 9/2000 |
| DE | 29824797 U1 | 8/2002 |
| EP | 0008780 A2 | 3/1980 |
| EP | 0 021 129 A2 | 5/1980 |
| EP | 0019253 A1 | 11/1980 |
| EP | 0035780 | 9/1981 |
| EP | 0141607 A2 | 5/1985 |
| EP | 0170360 A1 | 2/1986 |
| EP | 0193829 A2 | 9/1986 |
| EP | 0206417 A2 | 12/1986 |
| EP | 0 238 023 A2 | 9/1987 |
| EP | 0 326 026 A2 | 1/1989 |
| EP | 0304331 A2 | 2/1989 |
| EP | 0304332 A2 | 2/1989 |
| EP | 0 305 216 A1 | 3/1989 |
| EP | 0458845 A1 | 8/1990 |
| EP | 0458849 A1 | 8/1990 |
| EP | 0 407 225 A1 | 1/1991 |
| EP | 0600868 A1 | 12/1991 |
| EP | 0550450 A1 | 2/1992 |
| EP | 0592478 A1 | 1/1993 |
| EP | 0 583 726 A2 | 2/1994 |
| EP | 0691982 B1 | 1/1996 |
| EP | 0828509 A1 | 12/1996 |
| EP | 0 826 375 A2 | 3/1998 |
| EP | 0973878 A1 | 10/1998 |
| EP | 0897985 A2 | 2/1999 |
| EP | 1010423 A2 | 6/2000 |
| EP | 1138333 B1 | 4/2001 |
| EP | 1 186 658 A1 | 3/2002 |
| EP | 1 261 368 A2 | 12/2002 |
| EP | 1279402 A1 | 1/2003 |
| EP | 1593688 | 11/2005 |
| EP | 2278002 | 1/2011 |
| FR | 2 710 535 A1 | 4/1995 |
| GB | 1509866 | 5/1978 |
| JP | 04936885 A | 4/1974 |
| JP | 58148814 A | 9/1983 |
| JP | 58179492 | 10/1983 |
| JP | 59169491 A | 9/1984 |
| JP | 61162185 | 7/1986 |
| JP | 62-029950 | 2/1987 |
| JP | 04-023991 | 1/1992 |
| JP | 4187085 A | 7/1992 |
| JP | 8143457 A | 6/1996 |
| JP | 09125096 A | 5/1997 |
| WO | WO 82/03871 | 11/1982 |
| WO | 87/07292 A1 | 12/1987 |
| WO | 89/08694 A1 | 9/1989 |
| WO | 89/08695 A1 | 9/1989 |
| WO | 91/06638 A1 | 5/1991 |
| WO | 91/14454 A1 | 10/1991 |
| WO | WO 91/16060 | 10/1991 |
| WO | WO 91/18623 A1 | 12/1991 |
| WO | WO 92/02617 A1 | 2/1992 |
| WO | 92/12645 A1 | 8/1992 |
| WO | 92/13030 A1 | 8/1992 |
| WO | WO 93/00924 A1 | 1/1993 |
| WO | 93/07260 A1 | 4/1993 |
| WO | 93/07263 A1 | 4/1993 |
| WO | WO 94/08603 A1 | 4/1994 |
| WO | WO 94/08605 A1 | 4/1994 |
| WO | 95/07688 A1 | 3/1995 |
| WO | WO 95/08983 A1 | 4/1995 |
| WO | WO 95/15681 | 6/1995 |
| WO | 95/22625 A1 | 8/1995 |
| WO | 96/00343 A1 | 1/1996 |
| WO | 96/16151 A1 | 5/1996 |
| WO | 96/38527 A1 | 12/1996 |
| WO | WO 96/38170 A1 | 12/1996 |
| WO | 97/23605 A1 | 7/1997 |
| WO | 97/39116 A1 | 10/1997 |
| WO | WO 97/42980 | 11/1997 |
| WO | WO 98/00169 A1 | 1/1998 |
| WO | WO 98/38292 | 9/1998 |
| WO | WO 98/46732 A1 | 10/1998 |
| WO | WO 98/52561 A1 | 11/1998 |

(56) References Cited

FOREIGN PATENT DOCUMENTS

| | | |
|---|---|---|
| WO | WO 99/20745 | 4/1999 |
| WO | WO 99/28344 | 6/1999 |
| WO | WO 99/44589 A1 | 9/1999 |
| WO | 00/01793 A1 | 1/2000 |
| WO | WO 00/34510 | 6/2000 |
| WO | WO 00/54799 | 9/2000 |
| WO | WO 01/01960 A1 | 1/2001 |
| WO | 01/25412 A1 | 4/2001 |
| WO | WO 01/37808 A1 | 5/2001 |
| WO | 01/58276 A2 | 8/2001 |
| WO | WO 01/68139 A1 | 9/2001 |
| WO | 02/20746 A1 | 3/2002 |
| WO | 02/28369 A1 | 4/2002 |
| WO | WO 02/36156 | 5/2002 |
| WO | WO 02/40045 | 5/2002 |
| WO | WO 02/060474 A2 | 8/2002 |
| WO | WO 03/047595 A1 | 6/2003 |
| WO | 03/055967 A1 | 7/2003 |
| WO | 03/080827 A2 | 10/2003 |
| WO | WO 2004/007707 | 1/2004 |
| WO | 2004/069872 A1 | 8/2004 |
| WO | WO 2005/012911 | 2/2005 |
| WO | 2005/070962 A1 | 8/2005 |
| WO | WO 2005/092370 | 10/2005 |
| WO | 2006/044529 A1 | 4/2006 |
| WO | 2006/136159 A2 | 12/2006 |
| WO | 2007/020260 A2 | 2/2007 |
| WO | WO 2007/014896 | 2/2007 |
| WO | WO 2007/135125 | 11/2007 |
| WO | 2008/079685 A2 | 7/2008 |

OTHER PUBLICATIONS

Pariza M.W. & Johnson E.A.: "*Evaluating the safety of microbial enzyme preparations used in food processing: update for a new century*", Regul Toxicol Pharmacol. Apr. 2001; 33(2):173-86 (2001).
Subramanian R. & Wasan K.M. (2003) "*Effect of lipid excipients on in vitro pancreatic lipase activity*", Drug Dev. Ind. Pharm. 29(8): 885-890.
European Search Report dated Oct. 1, 2007 (five (5) pages).
Fiedler, Herbert P., (Lexikon der Hilfsstoffe fuer Pharmazie, Kosmetik and Angrenzende Gebiete, 5 Aufl. 2002), Encyclopedia of Excipients for Pharamceuticals, Cosmetics and Related Areas, vol. 5, pp. 773 and 995, including English translation (cover page, pp. 747 & 921). (Total: Six (6) pages), Printed and bound by R. Oldenbourg Graphische Betriebe Druckerei GmbH, Kirchheim, Germany.
Kreon® 25 000 (Magnified Photograph).
USP 32, NF 27, "Pancrelipase Delayed-Release Capsules."
2.9.1 Disintegration of Tablets and Capsules, European Pharmacopoeia 5.3, pp. 3351-3353.
21 C.F.R. 201.302 Notice to manufacturers, packers, and distributors of drugs for internal use which contain mineral oil.
ICH Harmonised Tripartite Guideline, Table of Content and pp. 1-16.
Nakamura, et al., Pancreas, vol. 16(3), pp. 329-336.
Ullman's Encyclopedia, pp. 175-176, 179, 180 and 199.
United States Pharmacopoeia Method 711 Dissolution (18 pages).
Carriere, et al., "Quantitative Study of Disgestive Enzyme Secretion and Gastrointestinal Lipolysis in Chronic Pancreatitis," Clinical Gastroenterology and Hepatology, vol. 3(1), pp. 28-38 (2005).
Delchier, et al., "Fate of Orally Ingested Enzymes in Pancreatic Insufficiency: Comparison of Two Pancreatic Enzyme Preparations," Aliment. Pharmacol. Therap., vol. 5, pp. 365-378 (1991).
Dimagno, et al., "Fate of Orally Ingested Enzymes in Pancreatic Insufficiency," The New England Journal of Medicine, vol. 296(23), pp. 1318-1322 (1977).
Dutta, et al., "Critical Examination of Therapeutic Efficacy of a pH-Sensitive Enteric-Coated Pancreatic Enzyme Preparation inTreatment of Exocrine Pancreatic Insufficiency Secondary to Cystic Fibrosis," Digestive Diseases and Sciences, vol. 33(10), pp. 1237-1244 (1988).
Gregory, P.C., "Gastrointestinal pH, Motility/Transit and Permeability in Cystic Fibrosis," J Pediatr Gastroenterol Nutr, vol. 23(5), pp. 513-523 (1996).
Guarner, et al., "Fate of Oral Enzymes in Pancreatic Insufficiency," Gut, vol. 34, pp. 708-712 (1993).
Keller, et al., "Human Pancreatic Exocrine Response to Nutrients in Health and Disease," Gut, vol. 54(Suppl. VI), pp. vi1-vi28 (2005).
Layer, et al., "Fate of Pancreatic Enzymes During Small Intestinal Aboral Transit in Humans," The American Physiology Society, pp. G475-G480 (1986).
Layer, et al., "Pancreatic Enzymes in Chronic Pancreatitis," International Journal of Pancreatology, Col. 15(1), pp. 1-11 (1994).
Sachs-Barrable, et al., "Lipid Excipients Peceol and Gelucire 44/14 Decrease P-Glycoprotein Mediated Efflux of Rhodamine 123 Partially Due to Modifying P-Glycoprotein Protein Expression within Caco-2 Cells," J Pharm Pharmaceut Sci, vol. 10(3), pp. 319-331 (2007).
Watkins, Paul, "The Barrier Function of CYP3A4 and P-Glycoprotein in the Small Bowel," Advanced Drug Delivery Reviews, vol. 27, pp. 161-170 (1997).
Archibald, A.L., "Comparison of the Serum Amylases of Farm Animals," Comp. Biochem. Physiol., vol. 88B (3), pp. 963-968 (1987).
Aquacoat ECD—FMC Biopolymer—Bulletin AECD-30-05/18/97. RS (1997).
Chueshov, et al., Industrial Technology of Drugs and Medicine, vol. 2, NFAU Publishing House, pp. 359-363 (2002) [with Translation].
Cunningham, L., "Reactivation of Diethyl p-Nitrophenyl Phosphate-Inhibited α-Chymotrypsin by Hydroxylamine," Journal of Biological Chemistry, vol. 207, pp. 443-458 (1954).
De Fiebre et al. "Elimination of *Salmonellae* from Animal Glandular Products," Applied Microbiology, vol. 17(3), pp. 344-346 (1969).
Estes, et al., "Proteolytic Enhancement of Rotavirus Infectivity: Molecular Mechanisms," Journal of Virology, vol. 39(3), pp. 879-888 (1981).
European Patent Appl. No. 06778012.2 Office Action dated Dec. 7, 2010 (5 pages).
Fang, et al., "Purification and Characterization of Adult Diarrhea Rotavirus: Identification of Viral Structural Proteins," Journal of Virology, vol. 63(5), pp. 2191-2197 (1989).
Federal Register, vol. 69(82), Part IV, Apr. 28, 2004.
Fiedler, Herbert P. Encyclopedia of Excipients for Pharmaceuticals, Cosmetics and Related Areas, 5th ed., pp. 1284-1287 (2002).
Hogan et al., Pharmaceutical Coating Technology, Chapter 14, pp. 409-439 (1995).
International Preliminary Report of Patentability for PCT/EP2008/065586 (May 18, 2010).
International Search Report for PCT/EP2008/065586 (Dec. 19, 2008).
International Search Report PCT/EP2009/050010 (May 7, 2009).
Jiang et al., "Biochemical Characterization of the Structural and Nonstructural Polypeptides of a Porcine Group C Rotavirus," Journal of Virology, vol. 64(7), pp. 3171-3178 (1990).
Keller, et al., "Pancreatic Enzyme Supplementation Therpay," Current Treatment Option in Gastroenterology, vol. 6, pp. 369-374 (2003).
Kobayashi, et al., "Susceptibility of Heptitis B Virus to Disinfectants or Heat," Journal of Clinical Microbiology, vol. 20(2), pp. 214-16 (1984).
Korzhavykh, et al., "Tablets and Their Various Forms", Russian Pharmacies, No. 19, pp. 1-5 (2010) [with Translation].
Kreon® 25000 Gebrauchsinformation (2007), English Translation.
Maunula, L., "Molecular Epidemiology of Human Rotaviruses—A Study in Genetic Diversity," Academic Dissertation, Haartman Institute, pp. 1-116, Helsinki 2001.
Material Safety Data Sheet, Pancreatin 4X USP (10X), Invitrogen Corp., pp. 1-7 (Rev. Apr. 16, 2005).
Michen, et al., "Isoelectric Points of Viruses," Journal of Applied Microbiology, vol. 109, pp. 388-397 (2010).
Naftifine HCI MSDS (Jun. 23, 2004), available at http://pharmacycide.com/msds/Naftifine_HCL.
Nilsson, et al., "Biosynthesis and morphogenesis of group C rotavirus in swine testicular cells," Arch. Virol., vol. 133, pp. 21-37 (1993).

(56) References Cited

OTHER PUBLICATIONS

Pharmaceutical Excipients, 5th ed., Cetyl Alcohol, pp. 155-156 (2006).
Register of Pharmaceuticals in Russia, RP-Pharmacist, Annual Collection, Issue 5, p. 772 (2003) [with Translation].
Remington, The Science and Practice of Pharmacy, 20th ed., pp. 326 and 1035-1036 (2000).
Saif et al., "Serial Propagation of Porcine Group C Rotavirus (Pararotavirus) in a Continuous Cell Line and Characterization of the Passaged Virus," Journal of Clinical Microbiology, vol. 26(7), pp. 1277-1282 (1988).
Sanekata, et al., "Isolation of Group B Porcine Rotavirus in Cell Culture," Journal of Clinical Microbiology, vol. 34(3), pp. 759-761 (1996).
Savage et al., "Determination of Adequate Moisture Content for Efficient Dry-Heat Viral Inactivation in Lyophilized Factor VIII Loss on Drying and by Near Infrared Spectroscopy," Biologicals, vol. 26, pp. 119-124 (1998).
Sofer, et al., "Part 6, Inactiviation Methods Grouped by Virus," BioPharm Internationals, S-37-42 (2003).
Sun et al., "Fluidized-bed spray coated porous hydrogel beads for sustained release of diclofenac sodium," Journal of Controlled Release, vol. 47, pp. 247-260 (1997).
The Ministry of Health, Labour and Welfare Ministerial Notification No. 285, Japan Pharmacopoeia, 8 pages (2006).
Thoma et al., "Influence of aqueous coatings on the stability of enteric coated pellets and tablets," European Journal of Pharmaceutics and Biopharmaceutics, vol. 47, pp. 39-50 A286(1999).
Tsunemitsu, et al., "Isolation, Characterization, and Serial Propagation of a Bovine Group C Rotavirus in a Monkey Kidney cell Line (MA104)," Journal of Clinical Microbiology, vol. 29(11), pp. 2609-2613 (1991).
United States Pharmacopoeia for Pancrelipase Delayed-Release Capsules (2 pages) (2006).
United States Pharmacopoeia Method 711 Dissolution (18 pages) (2006).
Walsh, et al., "Tryosinogen and Chymotrypsinogen as Homologous Proteins,". PNAS, vol. 52, pp. 884-889 (1964).
Wallis, et al., "Plaque Enhancement of Enteroviruses by Magnesium Chloride, Cysteine, and Pancreatin," Journal of Bacteriology, vol. 91(5), pp. 1932-1935 (1996).
Worthington Enzyme Manual, Lipase, (1993), pp. available at http://www.worthington-biochem.com/PL/default.html (2 pages).
Worthington Enzyme Manual, Trypsin (1993), available at http://www.worthington-biochem.com/TRY/default.html (3 pages).
Worthington Enzyme Manual, Trypsinogen (1993), available at http://www.worthingtonbiochem.com/TG/default.html (1 page).
Benzonana, et al., "Etude Cinetique de L'Action de la Lipase Pancreatique Sur Des Triglycerides en Emulsion Essai D'Une Enzymologie en Milieu Heterogene," Biochimica Et Biophysica ACTA, 105:121-136 (1965) (English Abstract).
Bezzine, et al., "Human Pancreatic Lipase: Colipase Dependence and Interfacial Binding of Lid Domain Mutants," Biochemistry, 23:5499-5510 (1999).
Borgstrom, et al., "Pancreatic Juice Co-Lipase: Physiological Importance," Biochimica Et Biophysica ACTA, 242:509-513 (1971).
Borgstrom, et al., "Pancreatic Lipase and Colipase: Interaction and Effect of Bile Salts and Other Detergents," Eur. J. Biochem, 37:60-68 (1973).
Borgstrom, "Binding of Pancreatic Colipase to Interfaces; Effects of Detergents," FEBS Letters, 71(2):201-204 (1976).
Borgstrom, "On the Interactions Between Pancreatic Lipase and Colipase and the Substrate and the Importance of Bile Salts," Journal of Lipid Research, 16:411-417 (1975).
EP 1931317, Aptalis Pharma S.r.L, Submission of Opponent 02 in Preparation of Oral Proceedings, Aug. 3, 2011.
EP 1931317, Nordmark Arzneimittel GmbH & Co. KG, Submission of Opponent 01 in Preparation of Oral Proceedings, Jul. 20, 2011 (with Translation).
Gargouri, et al., "Studies on the Detergent Inhibition of Pancreatic Lipase Activity," Journal of Lipid Research, 24:1336-1342 (1983).
Saunders, et al., "Lecithin Inhibits Fatty Acid and Bile Salt Absorption from Rat Small Intestine In Vivo," Lipids, 11 (12):830-832 (1976).
Ammon, et al., "Effect of Lecithin on Jejunal Absorption of Micellar Lipids in Man and on Their Monomer Activity in vitro," Lipds, 14(4):395-400 (1978).
Jones, et al., "Effects of Exogenous Emulsifiers and Fat Sources on Nutrient Digestibility, Serum Lipids, and Growth Performance in Weanling Pigs," J. Anim Sci., 70:3473-3482 (1992).
Kammlott, et al., "Experiments to Optimize Enzyme Substitution Therapy in Pancreatic Duct-Ligated Pigs," Journal of Animal Physiology and Animal Nutrition, 89:105-108 (2005).
Lukovac, et al., "Gelucire 44/14 Improves Fat Absorption in Rats with Impaired Lipolysis," Biochimica et Biophysica Acta, 1801:665-673 (2010).
O'Doherty, et al., "Role of Luminal Lecithin in Intestinal Fat Absorption," Lipids, 8(5):249-255 (1972).
Overland, et al., "Lecithin in Swine Diets: I. Weanling Pigs," J. Anim Sci, 71:1187-1193 (1993).
Overland, et al., "Effect of Lecithin on the Apparent Ileal and Overall Digestibility of Crude Fat and Fatty Acids in Pigs," J. Anim Sci, 72:2022-2028 (1994).
Tabeling, et al., "Studies on Nutrient Digestibilities (Pre-Caecal and Total) in Pancreatic duct-Ligated Pigs and the Effects of Enzyme Substitution," J. Anim. Physiol. A. Anim. Nutr., 82:251-263 (1999).
Copending U.S. Appl. No. 14/074,255, filed Nov. 7, 2013.
Brewer et al., "Porcine encephalomyocarditis virus persists in pig myocardium and infects human myocardial cells," J. Virology (2001) 75(23):11621-11629.
McLean et al., "Contamination detection in animal cell culture," Encyclopedia of Cell Technology (2000) 1-2:586-598.
United States Patent Office Action for U.S. Appl. No. 11/460,330 dated Oct. 18, 2013 (22 pages).
United States Patent Office Action for U.S. Appl. No. 11/751,497 dated Oct. 21, 2013 (13 pages).
Axcan Pharma, Inc., Viokase Prescribing Information, Mar. 2000, 3 pages.
Bieger, W. et al., "Two-dimensional isoelectric focusing/sodium dodecyl sulfate gel electrophoresis of protein mixtures containing active or potentially active proteases analysis of human exocrine pancreatic proteins," Anal. Biochem. (1980) 109:222-230.
Braeuniger, S. et al., "Further studies on thermal resistance of bovine parvovirus against moist and dry heat," Int. J. Hyg. Environ. Health (2000) 203:71-75.
Challapalli, K.K. et al., "High reproducibility of large-get two-dimensional electrophoresis," Electrophoresis (2004) 25:3040-3047.
Committee for Proprietary medicinal Products, Note for Guidance on Virus Validation Studies: The Design, Contribution and Interpretation of Studies Validating the Inactivation and Removal of Viruses, The European Agency for the Evaluation of Medicinal Products (Feb. 14, 1996) p. 1-13.
Cunningham, N. et al., "Replication of avian infectious bronchitis virus in African green monkey kidney cell line VERO," J. Gen. Virol. (1972) 16:423-427.
DeRobertis, Cell & Mol. Biol. (1980) 7th Ed., 132-133.
Directive 2003/36/EC of the European Parliament and of the Council of May 26, 2003, Official Journal of the European Union, p. L 156/26-30.
Definition of "picornaviridae," http://medical-dictionary.thefreedictionary.com/Picornaviridae, downloaded Jul. 26, 2011.
Dony, J. et al., "Etide electrophoretique et immunoelectrophoretique de preparations enzymatiques injectables: preparation d'origine pancreatique et preparations d'origine testiculaire," progress in Immunological Standardization (1970) 4:395-405, with English translation.
"Gastric juice" (http://www.thefreedictionary.com/gastric+juice) accessed Aug. 2, 2013.
Goerg, A et al., "The current state of two-dimensional electrophoresis with immobilized gH gradients," Electrophoresis (2000) 21:1037-1053.

(56) References Cited

OTHER PUBLICATIONS

Goldman, D. et al., "Human lymphocyte polymorphisms detected by quantitative two-dimensional electrophoresis," Am. J. Hum. Genet. (1983) 35:827-837.
Goodman & Gilman's "The Pharmacological Basis of Therapeutics," 8th Edition, Pergamon Press (1990) 1471-1477.
Jenkins, L.W. et al., "Conventional and functional proteomics using large formal two-dimensional gel electrophoresis 24 hours after controlled cortical impact in postnatal day 17 rats," J. Neurotrauma (2002) 19(6):715-740.
Kirk-Othmer, Encyclopedia of Chemical Technology, 3rd Edition, 23:724-25 (1984).
Klotz, H.P., "Lyophilized pancreatic extract, an aid in the treatment of mild diabetes," La Nouvelle Presse Medicals (1975) 4(32):2333, abstract.
Korneeva, O.S. et al., "Identification of catalytically active groups of wheat (*Triticum aestivum*) germ lipase," Appl. Biochem. & Microbiol. (2008) 44(4):349-355.
Lebowitz, J. et al., "Modern analytical ultracentrifugation in protein science: a tutorial review," Protein Sci. (2002) 11:2067-2079.
Marumerizer QJ-1000T Spheronizer (http://www.lcicorp.com/industrial_granulation/detail/category/marumerizer_qj1000 (accessed Jul. 26, 2013).
May et al., J. Biol. Standardization (1982) 10:249-259.
Meyer, Boyd Anal. Chem. (1959) 31:215-219.
Murlin et al., "The influence of alkili upon the glycos uria, hyperglycemia and carbon dioxide combining power in human diabetes," Proceedings of the Society for Experimental Biol. Med. (1917) 14:8-9.
Nishihara, J.C. et al., "Quantitative evaluation of proteins in one- and two-dimensional polyacrylamide gels using a fluorescent stain," Electrophoresis (2002) 23:2203-2215.
Padfield, P.J. et al., "The use of two-dimensional gel electrophoresis and high-performance liquid chromatography for the analysis of pancreatic juice," The Pancreas: Biology, Pathbiology, and Disease, Second Edition, Chapter 14 (1993) 265-273.
Porter, S.C., "Coating of pharmaceutical dosage forms," Chapter 46, Remington: The Science and Practice of Pharmacy, Lippincott, Williams & Wilkins, Philadelphia (2005) 21st Edition, Chapter 46:929-938.
Reed, L.J. et al., "A simple method of estimating fifty percent end points," Amer J. of Hygiene (1938) 27(3):493-497.
Ridder, G. et al., "Quantitative analysis of pattern recognition of two-dimensaional electrophoresis gels," Clin. Chem. (1984) 30(12):1919-1924.
Scharpe, S. et al., "Isoelectric characterization of porcine pancreative alpha amylases," Journal De Pharmacie De Belgique (1973) 28(6):705-708.
Scheele, G.A., "Two-dimensional gel analysis of soluble proteins," J. Biol. Chem. (1975) 250(14):5375-5385.
Shimura, K. et al., "Affinophoresis in two-dimensional agarose gel electrophoresis specific separation of biomolecules by a moving affinity ligand," Anal. Biochem. (1987) 161(1):200-206.
Smolka, M. et al., "Quantitative protein profiling using two-dimensional gel electrophoresis, isotope-coded affinity tag labeling, and mass spectrometry," Mol. Cell Proteomics (2002) 1.1:19-29.
Spearman, C., "The method of 'right and wrong cases' ('constant stimuli') without Gauss's formulae," Brit. J. Psych. (1908) vol. II, Part 3, 227-242.
Van Den Bergh, G. et al., "Fluorescent two-dimensional difference gel electrophoresis and mass spectrometry identify age-related protein expression differences for the primary visual cortex of kitten and adult cat," J. Neurochem. (2003) 85:193-205.
Veronese et al., "Photo inactivation of enzymes by linear and angular furocoumarins," Photochem & Photobiol. (1982) 36(1):25-30.
Villegas et al., "A rapid method to produce high yields of purified rotavirus particles," J. Virol. Meth. (2002) 104:9-19.
Voss, T. et al., "Observations on the reproducibility and matching efficiency of two-dimensional electrophoresis gels: consequences for comprehensive data analysis," Electrophoresis (2000) 21:3345-3350.
Wan et al., "Plasticizers and their effects on microencapsulation process by spray-drying in an aqueous sytem," J. Microencapsulation (1992) 9(1):53-62.
European Patent Office Search Report and Opinion for Application No. 07120740.1 dated Mar. 1, 2008.
European Patent Office Search Report for Application No. 10178590 dated Dec. 9, 2010.
European Patent Office Search Report and Preliminary Opinion for Application No. 06114329 dated Aug. 1, 2006.
European Search Report for Application No. 07120740.1 dated Mar. 3, 2008.
European Search Report for Application No. EP93112848 dated Apr. 15, 1994.
International Preliminary Report on Patentability for Application No. PCT/EP2004/008332 dated Jan. 30, 2006.
International Preliminary Report on Patentability for Application No. PCT/EP2006/064717 dated Oct. 11, 2007.
International Preliminary Report on Patentability for Application No. PCT/EP2006/065311 dated Feb. 20, 2008.
International Preliminary Report on Patentability for Application No. PCT/EP2006/065313 dated Feb. 20, 2008.
International Search Report and Written Opinion for Application No. PCT/EP2006/064717 dated Nov. 20, 2006.
International Search Report and Written Opinion for Application No. PCT/EP2006/065313 dated Feb. 2, 2007.
International Search Report and Written Opinion for Application No. PCT/EP2007/054880 dated Oct. 2, 2007.
International Search Report for Application No. PCT/EP2004/008332 dated Nov. 24, 2004.
International Search Report for Application No. PCT/EP2006/065311 dated Feb. 2, 2007.
International Search Report for Application No. PCT/EP2007/054880 dated Sep. 18, 2007.
Written Opinion for Application No. PCT/EP2006/065311 dated Feb. 2, 2007.
Written Opinion for Application No. PCT/EP2007/054880 dated Sep. 18, 2007.
United States Patent Office Action for U.S. Appl. No. 11/464,754 dated Sep. 2, 2009 (18 pages).
United States Patent Office Action for U.S. Appl. No. 11/464,754 dated Jun. 1, 2010 (16 pages).
United States Patent Office Action for U.S. Appl. No. 11/464,754 dated Aug. 16, 2013 (26 pages).
United States Patent Office Action for U.S. Appl. No. 11/460,330 dated Nov. 12, 2010 (13 pages).
United States Patent Office Action for U.S. Appl. No. 11/460,330 dated Aug. 4, 2011 (21 pages).
United States Patent Office Action for U.S. Appl. No. 11/460,330 dated Apr. 9, 2012 (21 pages).
United States Patent Office Action for U.S. Appl. No. 11/464,704 dated Aug. 21, 2009.
United States Patent Office Action for U.S. Appl. No. 11/464,704 dated May 26, 2010.
United States Patent Office Action for U.S. Appl. No. 11/464,704 dated Aug. 2, 2013 (21 pages).
United States Patent Office Action for U.S. Appl. No. 11/751,497 dated Nov. 12, 2009 (12 pages).
United States Patent Office Action for U.S. Appl. No. 11/751,497 dated Jul. 14, 2010.
United States Patent Office Action for U.S. Appl. No. 11/751,497 dated Mar. 10, 2011 (8 pages).
United States Patent Office Action for U.S. Appl. No. 11/751,497 dated Apr. 17, 2013 (16 pages).
United States Patent Office Action for U.S. Appl. No. 12/271,480 dated Nov. 3, 2010.
United States Patent Office Action for U.S. Appl. No. 12/271,480 dated Jul. 14, 2011 (12 pages).
United States Patent Office Action for U.S. Appl. No. 12/271,480 dated May 24, 2013 (14 pages).

(56) References Cited

OTHER PUBLICATIONS

United States Patent Office Action for U.S. Appl. No. 12/271,480 dated Sep. 19, 2013 (13 pages).
Chemical Abstract, No. 99:200535j, "Capsules Containing Stable Digestive Enzymes", vol. 99, p. 342 (1983).
D'Costa, D., "Diabetic Neuropathic Cachexia Associated with Malabsorption," Diabetic Medicine, vol. 9/2, pp. 203-205 (1992).
Delhaye, M., "Comparative Evaluation of a High Lipase Pancreatic Enzyme Preparation and a Standard Pancreatic Supplement for Treating Exocrine Pancreatic Insufficiency in Chronic Pancreatitis," European Journal of Gastronenterology and Hepatology, vol. 8/7, pp. 699-703 (1996).
European Search Report European Patent Application No. EP97114330 (Jun. 5, 2002).
Guidance for Industry SUPAC-MR, Modified Release Solid Oral Doage Form, pp. 1-36 (Sep. 1997).
International Preliminary Report of Patentability for PCT/EP2005/051295 (Apr. 4, 2006)).
International Search Report for PCT/EP2000/002261 (Jul. 11, 2000).
International Search Report and Written Opinion for PCT/EP2005/051295 (Jun. 24, 2005).
Nakamura, et al., Pancreas, vol. 16(3), pp. 329-336, 1998.
"Pancreatin", The American Heritage Dictionary of the English Language, 4th Edition Boston, Houghton Mifflin (2002). www.bartleby.com/61/ (printed Mar. 21, 2007).
"Pancreatin juice", The American Heritage Dictionary of the English Language, 4th Edition Boston, Houghton Mifflin (2002). www.bartleby.com/61/ (printed Mar. 21, 2007).
Simek, I., "Substitution Therapy in Insufficient External Pancreatic Secretion," Online Medline Databse (1993).
Thomson et al., Porcine Parvovirus Infection, Infectious Disease of Livestock, vol. 2, Ch. 73, (2nd edition), pp. 806-814 (2004).
Tischer et al., "Replication of procine circovirus: induction by glucosamine and cell cycle dependence," Archives of Virology, vol. 96, pp. 39-57 (1987).
Turner, et al., "The Inactivation of Viruses in Pig Slurries: A Review," Bioresource Technology, vol. 61, pp. 9-20 (1997).
Eurand S.A., Notice of Opposition against the European Patent No. EP 1931317., Sep. 23, 2009.
McGinity, Aqueous Polymeric Coatings for Pharmaceutical Dosage, Marcel Dekker, Inc.,1989.
Murthy, et al., "In Vitro Release Characteristics of Hard Shell Capsule Products Coated with Aqueous- and Organic-Based Enteric Polymers," Journal of Biomaterials Application, J. Biomater Appl., vol. 3, pp. 52-79 (1988), available at http://jba.sagepub.com.
Nordmark Arzneimittel GmbH & Co. KG, Notice of Opposition against the European Patent No. EP 1931317., Aug. 6, 2009 with translation.
Oshima, et al., "Preparation of Rapidly Disintegrating Tablets Containing Itraconazole Solids Dispersion," Chem. Pharm. Bull., vol. 55(11), pp. 1557-1562 (2007).
Reynolds, "A New Technique for the Production of Spherical Particles," Manufact. Chemist & Aerosol News, pp. 40-43 (Jun. 1970).
Sucker et al., "Pharmazeutische Techologie," pp. 273-283 (1991) with translation.
U.S. Patent Office Action for U.S. Appl. No. 11/464,754 dated Apr. 23, 2014 (31 pages).
U.S. Patent Office Action for U.S. Appl. No. 11/460,330 dated Jun. 2, 2014 (23 pages).
U.S. Patent Office Action for U.S. Appl. No. 11/464,704 dated Apr. 25, 2014 (25 pages).

\* cited by examiner

PHARMACEUTICAL COMPOSITIONS OF LIPASE-CONTAINING PRODUCTS, IN PARTICULAR OF PANCREATION

CROSS REFERENCE TO RELATED APPLICATIONS

This application claims priority from U.S. provisional patent application No. 60/554,993, filed Mar. 22, 2004, the entire disclosure of which is incorporated herein by reference. Convention priority is also claimed based on European patent application no. 04 10 1164.4, filed Mar. 22, 2004, the disclosure of which is likewise incorporated by reference herein.

BACKGROUND OF THE INVENTION

The invention relates to novel pharmaceutical compositions of lipase-containing products for oral administration, in particular pancreatin and pancreatin-containing products, or of enzyme products containing at least one lipase of non-animal, especially microbial origin, in which the pharmaceutical compositions provide improved lipolytic activity, in particular a stabilization of the lipase in the acidic pH range. These novel pharmaceutical compositions contain a system which comprises at least one surfactant and one co-surfactant, and are self-emulsifiable on contact with a hydrophilic and a lipophilic phase. The pharmaceutical compositions of the invention are well suited for the treatment and/or inhibition of maldigestion, in particular maldigestion based on chronic exocrine pancreatic insufficiency, in mammals and humans.

Maldigestion in mammals and humans is usually based on a deficiency of digestive enzymes, in particular on a deficiency of endogenous lipase, but also of protease and/or amylase. The cause of such a deficiency of digestive enzymes is frequently a hypofunction of the pancreas (=pancreatic insufficiency), the organ which produces the most, and the most important, endogenous digestive enzymes. If the pancreatic insufficiency is pathological, this may be congenital or acquired. Acquired chronic pancreatic insufficiency may, for example, be ascribed to alcoholism. Congenital pancreatic insufficiency may, for example, be ascribed to the congenital disease cystic fibrosis. Consequences of the deficiency of digestive enzymes may include severe symptoms of under-nutrition and malnutrition, which may be accompanied by increased susceptibility to secondary illnesses.

Substitution with similarly-acting exogenous digestive enzymes or mixtures of digestive enzymes has proved effective treatment for a deficiency in endogenous digestive enzymes. At present, pharmaceutical preparations (=preparations) which contain porcine pancreatin (=pancreatin) are frequently used for this purpose. Such mixtures of digestive enzymes obtained from the pig pancreas comprise lipases, amylases and proteases, and can be used effectively for enzyme substitution therapy in humans due to the great similarity of the enzymes and accompanying substances contained therein to the contents of human pancreatic juices. For example, processes are described in U.S. Pat. No. 4,019,958 (=DE 25 12 746) and German Patent Publication No. DE 42 03 315 by which pancreatin is obtained as a natural enzyme mixture by extraction from porcine pancreas and subsequently is converted in a known manner into the desired pharmaceutical form. The pancreatic enzymes are usually administered orally in the form of solid preparations. Pancreatin is thus commercially available, for example under the trade name Kreon®, in the form of granules, pellets or capsules with enteric-coated micropellets.

In order that, when taken orally, the administered enzyme mixtures are not irreversibly denatured in the stomach by gastric acid and proteolytic enzymes, such as pepsin present there, it is necessary to provide the enzyme mixtures with an enteric coating. Such a coating enables the enzyme mixtures to pass intact through the stomach to their point of action, the duodenum, where, due to the neutral to slightly alkaline conditions prevailing there, the protective layer is broken down and the enzymes are released. Like the endogenous pancreatic enzymes of healthy humans, the orally supplied enzymes can exert their enzymatic action, in particular amylolytic, lipolytic and proteolytic activity, there. Such solid pancreatin formulations which can be coated with an enteric film are described e.g. in U.S. Pat. No. 4,280,971 (=EP 21, 129).

U.S. Pat. No. 5,378,462 (=EP 583,726) describes pancreatin micropellet cores coatable with an enteric film having a pancreatin content of 65-85%, in particular 75-80%, by weight which have a bulk density of 0.6 g/ml to 0.85 g/ml, consisting essentially of pancreatin, polyethylene glycol 4000 and low-viscosity paraffin, containing per 100 parts by weight pancreatin: 15-50, in particular 20-30, parts by weight polyethylene glycol 4000; and 1.5-5, in particular 2-3, parts by weight low-viscosity paraffin, and having a spherical to ellipsoid form, the sphere diameter or the minor axis being in the range of 0.7-1.4 mm, in particular 0.8-1.2 mm, and having a particle-size distribution in which at least 80% of the pancreatin micropellet cores have a ratio of minor axis to major axis in the range of 1:1 to 1:2.

Furthermore, U.S. Pat. No. 5,993,806 (=EP 826,375) describes the use of lecithin as a stabilizing agent added to water-soluble pharmaceutical preparations of mixtures of digestive enzymes which contain protease/lipase mixtures, in particular pancreatin, and which are suitable for the preparation of aqueous solutions for continuous introduction into the gastrointestinal tract via probes. The lecithin is added to stabilize the mixtures of digestive enzymes against a decrease in the lipolytic activity under the influence of moisture.

In the case of pharmaceutical formulations not coated with enteric films, it is known that at the point of action of the enzymes, in the duodenum, often only a very small proportion of the lipase contained in the pharmaceutical preparation and taken therewith is active. Thus in German Patent Publication No. DE 36 42 853 such enzyme deactivation is ascribed to insufficient neutralization of the gastric acid in the duodenum. Whereas in a healthy human the postprandial intraduodenal pH value is about 6, patients with pancreatic insufficiency only have a pH value of about 4. At this pH value, the lipase contained in the pharmaceutical preparation has only one fifth of the activity that it would otherwise have at a pH value of 6.

SUMMARY OF THE INVENTION

It is therefore an object of the invention to provide pharmaceutical compositions which contain enzymes or enzyme mixtures with at least lipolytic activity and have improved lipolytic activity and in particular show a stabilization of the lipase activity in the acidic pH range.

According to the invention, pharmaceutical compositions intended for oral administration are provided which comprise enzymes or enzyme mixtures with at least lipolytic activity and a system comprising at least one surfactant and at least one co-surfactant. The pharmaceutical compositions of the invention are characterized in that they form emulsions upon contact with a hydrophilic phase and a lipophilic phase. Preferably the hydrophilic phase used to form the final emulsion after ingestion of the pharmaceutical composition is supplied by the physiological fluid of the digestive milieu. In a further embodiment of the present invention, the lipophilic phase used to form the final emulsion in the digestive tract after ingestion of the pharmaceutical composition is at least partially supplied by the lipids present in the food ingested. In particular, to achieve this object the invention provides pharmaceutical compositions which contain systems which comprise at least one surfactant, one co-surfactant and a lipophilic phase.

Surprisingly, a lipase-containing pharmaceutical composition containing such a system has improved lipolytic activity and a lipolytic activity which is stabilized in the acidic pH range. The use of such a system in pharmaceutical compositions of enzymes or enzyme mixtures with at least lipolytic activity furthermore has the advantage that pharmaceutical compositions containing such enzymes or enzyme mixtures can also be used without enteric coatings, such as are described for example in U.S. Pat. No. 5,378,462. In the pharmaceutical compositions according to the invention the reduction in the lipolytic activity during passage through the stomach is very much less than with pharmaceutical compositions prepared without the aforementioned system. The system consisting of surfactant, co-surfactant and optionally a lipophilic phase, stabilizes the lipolytic activity of the pharmaceutical compositions according to the invention in the acidic pH range of the stomach compared with conventional formulations.

The fact that the use of such enteric-coated polymer films and softeners which are otherwise necessary for film-coating various medicament forms (granules, pellets, mini-tablets, tablets etc.) can be omitted in the preparation of the lipase-containing compositions according to the invention yields further advantages. Thus the safety profile of the pharmaceutical composition is improved by omitting the enteric polymer films and softeners, since unnecessary taking thereof is avoided. Furthermore, the proportions of the amount of film-coating material in the medicament forms provided with an enteric film is approx. 20-30% of the entire weight of the medicament form. The ability to omit these additives makes the amount of pharmaceutical composition to be taken smaller, which results in better acceptance by patients.

The possibility of omitting enteric coating of the enzymes or enzyme mixtures furthermore has the advantage that thorough mixing of the pharmaceutical preparation with the chyme can take place as early as in the stomach. Thereupon, there forms an emulsion or micro-emulsion with enlarged surface, on which the lipase contained in the pharmaceutical composition is distributed such that it is given optimum possibilities for attack for breaking down the triglycerides found in the chyme. The formation of emulsion and microemulsion is further intensified by the lipolytic breakdown of the triglycerides to form di- and monoglycerides and free fatty acids. The improved possibilities of attack for the lipase thus result in intensified breakdown of the triglycerides. The higher concentration of free fatty acids resulting from the food provided in this way results in better fat absorption in the duodenum. In vitro, an increase in the lipolytic activity by about 10% compared with conventional lipase-containing pharmaceutical preparations was determined for the pharmaceutical composition according to the invention. The pharmaceutical compositions according to the invention thus exhibit stabilization of the lipolytic activity in the stomach as well as in the duodenum. Additionally, due to the intensified formation of a (micro)emulsion, the lipolytic activity is increased. The (micro)emulsion already produced independently in the stomach results in better activation of the lipase contained in the pharmaceutical composition.

Self-emulsifying pharmaceutical compositions in general are already known from the prior art. Thus, for example, U.S. Pat. No. 6,054,136 (=EP 670,715) describes a perorally administered composition which is suitable for forming a microemulsion in situ with the biological liquid of the organism and thus is said to improve the biological availability of an active substance. Such pharmaceutical compositions are known under the term SMEDDS® (Self Microemulsifying Drug Delivery System) and consist in principle of a mixture of one or more active substances with a defined lipophilic phase, a defined surfactant and a defined co-surfactant, the properties of which are specified such that the end product is capable of forming a microemulsion on contact with a given volume of physiological liquid.

Furthermore, U.S. 2003/021844 (=EP 1,058,540) describes what is called a SMEDDS® formulation in a particular pharmaceutical form, which is referred to as "pellet". These pellets are composed of an active substance, in particular indomethacin, a binding agent which is suitable for improving the biological availability of the active substance, for example Gelucire® 44/14, and a diluent, for example lactose, in micronized form.

The object of prior art systems which automatically form a microemulsion was, however, always to increase the bioavailability of mostly lipophilic active substances in that the SMEDDS® formulation, as a result of the micelle formation, permits better absorption of the active substance through the duodenal wall into the blood circulation. In contrast, the aim of the present invention is to provide a pharmaceutical composition which does not contain any lipophilic active substances to be absorbed into the bloodstream, but which provides as active agent enzymes or enzyme mixtures with at least lipolytic activity which develop their action in the gastrointestinal tract. The self-emulsifiable pharmaceutical compositions according to the invention result in a surprising increase of the lipolytic activity contained therein and in an improved stability of the lipase in the acidic pH range. Such pharmaceutical compositions of lipase-containing enzyme products which are self-emulsifiable on contact with a hydrophilic phase and which comprise a system consisting of a surfactant, a co-surfactant and optionally a lipophilic phase have not been described in the prior art.

Subramanian and Wasan describe an assay in which they demonstrate that the substance Gelucire® 44/14 in vitro has an inhibiting effect on the pancreatic lipase activity [Subramanian R. & Wasan K. M. (2003) "Effect of lipid excipients on in vitro pancreatic lipase activity" Drug Dev. Ind. Pharm. 29(8): 885-90]. In this experiment, a particular lipid-containing assay buffer with separate solutions of Gelucire® 44/14, pancreatic lipase and co-lipase is mixed, and the influence of Gelucire® on the lipase activity is measured. Since the lipase activity decreases, the authors conclude that Gelucire® and similar lipidic additions to pharmaceutical formulations can have an adverse effect on the in vitro activity of the pancreatic lipase. In contrast, the present invention shows that self-emulsifiable pharmaceutical compositions consisting of lipase-containing enzyme mixtures and a system such as for example Gelucire® 44/14 result in an increase in the lipolytic activity contained in the pharmaceutical formulation.

Some expressions as used in the context of the present invention are explained in more detail below.

The "hydrophilic-lipophilic balance" (=HLB) value is an empirical parameter commonly used to characterize the relative hydrophilicity and lipophilicity of non-ionic amphiphilic compounds. Surfactants or co-surfactants with lower HLB values are more lipophilic and have greater solubility in oils, whereas surfactants or co-surfactants with higher HLB values are more hydrophilic and have greater solubility in aqueous solutions. It should be kept in mind that for anionic, cationic, or zwitterionic compounds the HLB scale is not generally applicable.

Generally, the HLB value of a surfactant or co-surfactant is a practical guide used to enable formulation of industrial, pharmaceutical and cosmetic emulsions. However, for many important surfactants, including several polyethoxylated surfactants, it has been reported that HLB values can differ by as much as about 8 HLB units depending upon the empirical method chosen to determine the HLB value [Schott, J. Pharm. Sciences, 79(1), 87-88 (1990)]. Likewise, for certain polypropylene oxide containing block copolymers (poloxamers), the HLB values may not accurately reflect the true physical/chemical nature of the compounds. Finally, commercial surfactant and/or co-surfactant products are generally not pure compounds, but are often complex mixtures of compounds, and the HLB value reported for a particular compound may more accurately be characteristic of the commercial product of which the compound is a major component. Different commercial products having the same primary surfactant and/or co-surfactant component can, and typically do, have different HLB values. In addition, a certain amount of lot-to-lot variability is expected even for a single commercial surfactant and/or co-surfactant product.

A "surfactant" in the context of the present invention is a chemical compound comprising two groups, the first being hydrophilic and/or polar or ionic and having a high affinity for water, and the second containing an aliphatic chain of greater or lesser length and being hydrophobic (lipophilic); i.e., a surfactant compound must be amphiphilic. These chemical compounds are intended to cause the formation and stabilization of oil-in-water emulsions. Surfactants with lower HLB values are more lipophilic and have greater solubility in oils, whereas surfactants with higher HLB values are more hydrophilic and have greater solubility in aqueous solutions. Suitable surfactants in the context of the present invention have an HLB value above 6 and below 18, preferably above 8 and below 16. Surfactants can be any surfactant suitable for use in pharmaceutical compositions. Suitable surfactants can be anionic, cationic, zwitterionic or non-ionic. Such surfactants can be grouped into some general chemical classes as explained below. It should be emphasized that the invention is not limited to the surfactants indicated herein, which show representative, but not exclusive, lists of available surfactants.

"PEG-Fatty Acid Monoester Surfactants": Although polyethylene glycol (PEG) itself does not function as a surfactant, a variety of PEG-fatty acid esters have useful surfactant properties. Particularly preferred are PEG-fatty acid monoesters with aliphatic $C_6$-$C_{22}$ carboxylic acids, in which the polyethylene glycol comprises 6 to 60 ethylene oxide units per molecule. Examples of commercially available polyethoxylated fatty acid monoester surfactants include: PEG-4 laurate, PEG-4 oleate, PEG-4 stearate, PEG-5 stearate, PEG-5 oleate, PEG-6 oleate, PEG-7 oleate, PEG-6 laurate, PEG-7 laurate, PEG-6 stearate, PEG-8 laurate, PEG-8 oleate, PEG-8 stearate, PEG-9 oleate, PEG-9 stearate, PEG-10 laurate, PEG-10 oleate, PEG-10 stearate, PEG-12 laurate, PEG-12 oleate, PEG-12 ricinoleate, PEG-12 stearate, PEG-15 stearate, PEG-15 oleate, PEG-20 laurate, PEG-20 oleate, PEG-20 stearate, PEG-25 stearate, PEG-32 laurate, PEG-32 oleate, PEG-32 stearate, PEG-30 stearate, PEG 4-100 monolaurate, PEG 4-100 monooleate, and PEG 4-100 monostearate.

"PEG-Fatty Acid Diester Surfactants": Polyethylene glycol (PEG) fatty acid diesters are also suitable for use as surfactants in the compositions of the present invention. Particularly preferred are PEG-fatty acid diesters with aliphatic $C_6$-$C_{22}$ carboxylic acids in which the polyethylene glycol comprises 6 to 60 ethylene oxide units per molecule. Representative commercially available PEG-fatty acid diesters include: PEG-4 dilaurate, PEG-4 dioleate, PEG-6 dilaurate, PEG-6 dioleate, PEG-6 distearate, PEG-8 dilaurate, PEG-8 dioleate, PEG-8 distearate, PEG-10 dipalmitate, PEG-12 dilaurate, PEG-12 distearate, PEG-12 dioleate, PEG-20 dilaurate, PEG-20 dioleate, PEG-20 distearate, PEG-32 dilaurate, PEG-32 dioleate, and PEG-32 distearate.

"PEG-Fatty Acid Mono- and Di-ester Mixtures": In general, mixtures of surfactants are also useful in the present invention, including mixtures of two or more commercial surfactant products. Particularly preferred are mixtures of PEG-fatty acid mono- and diesters with aliphatic $C_6$-$C_{22}$ carboxylic acids in which the polyethylene glycol comprises 6 to 60 ethylene oxide units per molecule. Several PEG-fatty acid esters are marketed commercially as mixtures or mono- and diesters. Representative commercially available surfactant mixtures include: PEG 4-150 mono, dilaurate; PEG 4-150 mono, dioleate; and PEG 4-150 mono, distearate.

"Polyethylene Glycol (PEG) Glycerol Fatty Acid Esters": In addition, PEG glycerol fatty acid esters suitable as surfactants in the context of the present invention include: PEG-20 glyceryl laurate, PEG-30 glyceryl laurate, PEG-15 glyceryl laurate, PEG-40 glyceryl laurate, PEG-20 glyceryl stearate, PEG-20 glyceryl oleate, and PEG-30 glyceryl oleate. Particularly preferred are PEG glycerol fatty acid esters with aliphatic $C_6$-$C_{22}$ carboxylic acids in which the polyethylene glycol comprises 6 to 60 ethylene oxide units per molecule.

"Polyethylene Glycol (PEG) Alkyl Ethers (mono- and/or diethers of polyethylene glycol)": Ethers of polyethylene glycol and alkyl alcohols also are suitable surfactants for use in the present invention. Particularly preferred are PEG-fatty acid mono- and/or diethers with aliphatic $C_{12}$-$C_{18}$ alcohols in which the polyethylene glycol comprises 6 to 60 ethylene oxide units per molecule. Some commercially available examples of these surfactants include: PEG-2 oleyl ether (oleth-2), PEG-3 oleyl ether (oleth-3), PEG-5 oleyl ether (oleth-5), PEG-10 oleyl ether (oleth-10), PEG-20 oleyl ether (oleth-20), PEG-4 lauryl ether (laureth-4), PEG-9 lauryl ether, PEG-23 lauryl ether (laureth-23), PEG-2 cetyl ether, PEG-10 cetyl ether, PEG-20 cetyl ether, PEG-2 stearyl ether, PEG-10 stearyl ether, and PEG-20 stearyl ether.

"Polyethylene Glycol Sterol Ethers": PEG-derivatives of sterols are suitable surfactants for use in the present invention. Examples of surfactants of this class include: PEG-24 cholesterol ether, PEG-30 cholestanol, PEG-25 phytosterol, PEG-5 soya sterol, PEG-10 soya sterol, PEG-20 soya sterol, and PEG-30 soya sterol.

"Polyethylene Glycol Sorbitan Fatty Acid Esters": A variety of PEG-sorbitan fatty acid esters are available and are suitable for use as surfactants in the present invention. Examples of these surfactants include: PEG-10 sorbitan laurate, PEG-20 sorbitan monolaurate, PEG-4 sorbitan monolaurate, PEG-80 sorbitan monolaurate, PEG-6 sorbitan monolaurate, PEG-20 sorbitan monopalmitate, PEG-20 sorbitan monostearate, PEG-4 sorbitan monostearate, PEG-8 sorbitan monostearate, PEG-6 sorbitan monostearate, PEG-20 sorbitan tristearate, PEG-60 sorbitan tetrastearate, PEG-5 sorbitan monooleate, PEG-6 sorbitan monooleate, PEG-20 sorbitan monooleate, PEG-40 sorbitan oleate, PEG-20 sorbitan trioleate, PEG-6 sorbitan tetraoleate, PEG-30 sorbitan tetraoleate, PEG-40 sorbitan tetraoleate, PEG-20 sorbitan monoisostearate, and PEG sorbitol hexaoleate.

"Sugar Esters": Esters of sugars, in particular mono-esters are suitable surfactants for use in the present invention. Examples of such surfactants include: sucrose distearate/ monostearate, sucrose dipalmitate, sucrose monostearate, sucrose monopalmitate, sucrose monolaurate, and saccharose monolaurate.

"Polyoxyethylene-Polyoxypropylene Block Copolymers": The POE-POP block copolymers are a unique class of polymeric surfactants. The unique structure of the surfactants, with hydrophilic POE and lipophilic POP moieties in well-defined ratios and positions, provides a wide variety of surfactants suitable for use in the present invention. The generic term for these polymers is "poloxamer" (CAS 9003-11-6). These polymers have the formula: $HO(C_2H_4O)_a(C_3H_6O)_b(C_2H_4O)_aH$, where "a" and "b" denote the number of polyoxyethylene and polyoxypropylene units, respectively.

Furthermore, "amphoteric compounds" such as fatty acid-amidoalkyl betaines with $C_2$-$C_{22}$ fatty acids are suitable surfactants.

The surfactant can also be, or include as a component, an "ionic surfactant," including cationic, anionic and zwitterionic surfactants. Preferred anionic surfactants include fatty acid salts and bile salts. Preferred cationic surfactants include carnitines. Specifically, preferred ionic surfactants include sodium oleate, sodium lauryl sulfate, sodium lauryl sarcosinate, sodium dioctyl sulfosuccinate, sodium cholate, sodium taurocholate; lauroyl carnitine; palmitoyl carnitine; myristoyl carnitine, alginate salts; propylene glycol alginate; lecithins and hydrogenated lecithins; lysolecithin and hydrogenated lysolecithins; lysophospholipids and derivatives thereof; phospholipids and derivatives thereof; salts of alkylsulfates; sodium docusate; carnitines; and mixtures thereof.

More specifically, examples of preferred ionic surfactants include lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidylinositol, lysophosphatidic acid, lysophosphatidylserine, PEG-phosphatidylethanolamine, PVP-phosphatidylethanolamine, stearoyl-2-lactylate, stearoyl lactylate, cholate, taurocholate, glycocholate, deoxycholate, taurodeoxycholate, chenodeoxycholate, glycodeoxycholate, glycochenodeoxycholate, taurochenodeoxycholate, ursodeoxycholate, tauroursodeoxycholate, glycoursodeoxycholate, cholylsarcosine, N-methyl taurocholate, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

A "co-surfactant," sometimes also referred to as a "co-emulsifier", in the context of the present invention is a chemical compound which has both hydrophobic (lipophilic) and hydrophilic portions, but with the hydrophobic (lipophilic) nature predominating. It is intended to make the aqueous and oily phases in a microemulsion mutually soluble. Suitable co-surfactants in the context of the present invention have an HLB value below 10, preferably below 8 and even more preferably below 6. Co-surfactants can be any partial esters and/or partial ethers of polyhydric (polyvalent) alcohols, such as glycerol, propylenglycol (1,2-propanediol; 1,2-dihdroxypropane), ethyl-diglycol or even polyglycerols (such as diglycerol, triglycerol, tetraglycerol etc.) with aliphatic carboxylic acids (fatty acids) or aliphatic alcohols (fatty alcohols).

Further co-surfactants, which can be grouped into some general chemical classes, are given below. It should be emphasized that the invention is not limited to the co-surfactants mentioned herein, which show representative, but not exclusive, lists of available co-surfactants.

"Mono-glycerides": A particularly important class of co-surfactants is the class of mono-glycerides which are generally lipophilic. Particulary preferred are mixtures of monoglycerides with aliphatic $C_6$-$C_{22}$ carboxylic acids. Examples of this class of co-surfactants include: monopalmitolein (C16:1), monoelaidin (C18:1), monocaproin (C6), monocaprylin, monocaprin, monolaurin, glyceryl monomyristate (C14), glyceryl monooleate (C18:1), glyceryl monooleate, glyceryl monolinoleate, glyceryl ricinoleate, glyceryl monolaurate, glyceryl monopalmitate, glyceryl monostearate, glyceryl monopalmate, glycerol monostearate, glyceryl caprylate, and glyceryl caprate as well as mixtures thereof.

"Polyglycerized Fatty Acids": Polyglycerol esters of fatty acids, in particular Polyglycerol mono-esters, are also suitable co-surfactants for the present invention. Particulary preferred are mixtures of polyglycerol esters with aliphatic $C_6$-$C_{22}$ carboxylic acids. Examples of suitable commercially available polyglyceryl esters include: polyglyceryl-2 stearate, polyglyceryl-2 oleate, polyglyceryl-2 isostearate, polyglyceryl-3 oleate, polyglyceryl-4 oleate, polyglyceryl-4 stearate, polyglyceryl-6 oleate, polyglyceryl-2 dioleate and polyglyceryl-6 dioleate.

"Propylene Glycol Fatty Acid Esters": Partial esters of propylene glycol and fatty acids, in particular mono-esters, are suitable co-surfactants for use in the present invention. Particularly preferred are mixtures of propylene glycol esters with aliphatic $C_6$-$C_{22}$ carboxylic acids. Examples of co-surfactants of this class include: propylene glycol monocaprylate, propylene glycol monolaurate, propylene glycol oleate, propylene glycol myristate, propylene glycol monostearate, propylene glycol hydroxy stearate, propylene glycol ricinoleate, propylene glycol isostearate, propylene glycol monooleate, propylene glycol dicaprylate/dicaprate, propylene glycol dioctanoate, propylene glycol caprylate/caprate, propylene glycol dilaurate, propylene glycol distearate, propylene glycol dicaprylate, and propylene glycol dicaprate.

A "lipophilic phase" in the context of the present invention is understood to mean a water-immiscible liquid. The lipophilic phase may also be referred to as a lipidic phase. For compositions of the present invention in which the system also includes a lipophilic component, the lipophilic component is preferably a triglyceride or a mixture of a triglyceride and a diglyceride. Suitable lipophilic phases are preferably di- and triacylglycerides of aliphatic carboxylic acids (fatty acids) with 4 to 22 carbon atoms, in particular with 6 to 22 carbon atoms, and also mixtures thereof.

Preferred "di-glycerides" in the context of the present invention are mixtures of diglycerides with aliphatic $C_6$-$C_{22}$ carboxylic acids. Examples include: glyceryl dioleate, glyceryl dipalmitate, glyceryl dilaurate, glyceryl dilinoieate, glyceryl dicaprylate, glyceryl dicaprate, glyceryl caprylate/caprate, glyceryl distearate, glyceryl stearate/palmitate, glyceryl oleate/linoleate and glyceryl dimyristate.

Preferred "triglycerides" are those which solidify at ambient room temperature, with or without addition of appropriate additives, or those which in combination with particular surfactants and/or co-surfactants and/or active ingredients solidify at room temperature. Examples of triglycerides suitable for use in the present invention include: aceituno oil, almond oil, araehis oil, babassu oil, beeswax, black currant seed oil, borage oil, buffalo ground oil, candlenut oil, canola oil, castor oil, Chinese vegetable tallow oil, cocoa butter, coconut oil, coffee seed oil, corn oil, cottonseed oil, *crambe* oil, *cuphea* species oil, evening primrose oil, grapeseed oil, groundnut oil, hemp seed oil, illipe butter, kapok seed oil, linseed oil, menhaden oil, mowrah butter, mustard seed oil, oiticica oil, olive oil, palm oil, palm kernel oil, peanut oil, poppy seed oil, rapeseed oil, rice bran oil, safflower oil, sal fat, sesame oil, shark liver oil, shea nut oil, soybean oil, stillingia oil, sunflower oil, tall oil, tea seed oil, tobacco seed oil, tung oil (China wood oil), ucuhuba, vernonia oil, wheat germ oil, hydrogenated castor oil, hydrogenated coconut oil, hydrogenated cottonseed oil, hydrogenated palm oil, hydrogenated soybean oil, hydrogenated vegetable oil, hydrogenated cottonseed and castor oil, partially hydrogenated soybean oil, partially hydrogenated soy and cottonseed oil, glyceryl mono-, di-, tri-behenate, glycerol tributyrate, glyceryl tricaproate, glyceryl tricaprylate, glyceryl tricaprate, glyceryl triundecanoate, glyceryl trilaurate, glyceryl trimyristate, glyceryl tripalmitate, glyceryl tristearate, glyceryl triarchidate, glyceryl trimyristoleate, glyceryl tripalmitoleate, glyceryl trioleate, glyceryl trilinoleate, glyceryl trilinolenate, glyceryl tricaprylate/caprate, glyceryl tricaprylate/caprate/laurate, glyceryl tricaprylate/caprate/linoleate, glyceryl tricaprylate/caprate/stearate, glyceryl tricaprylate/laurate/stearate, glyceryl 1,2-caprylate-3-linoleate, glyceryl 1,2-caprate-3-stearate, glyceryl 1,2-laurate-3-myristate, glyceryl 1,2-myristate-3-laurate, glyceryl 1,3-palmitate-2-butyrate, glyceryl 1,3-stearate-2-caprate, glyceryl 1,2-linoleate-3-caprylate.

Fractionated triglycerides, modified triglycerides, synthetic triglycerides, and mixtures of triglycerides are also within the scope of the invention. Preferred triglycerides include vegetable oils, fish oils, animal fats, hydrogenated vegetable oils, partially hydrogenated vegetable oils, medium and long-chain triglycerides, and structured triglycerides.

Furthermore, the following compounds may be suitable as "liophilic phase": low-viscosity and high-viscosity aliphatic hydrocarbons, and also in particular oleic acid oleyl ester, isooctyl stearate, lauric acid hexyl ester, di-n-butyl adipate, isopropyl myristate, isopropyl palmitate and isopropyl stearate, oleyl alcohol, ethereal oils, isopropyl caprylate, isopropyl caprinate and isopropyl laurate.

"Complete Systems Composed of Surfactant, Co-Surfactant and Lipophilic Phase"

Several commercial surfactant and/or co-surfactant compositions contain small to moderate amounts of di- and triglycerides, typically as a result of incomplete reaction of a triglyceride starting material in, for example, a transesterification reaction. Such commercial surfactant and/or co-surfactant compositions, while nominally referred to as "surfactants" and/or "co-surfactant", may be suitable to provide—in addition to the surfactant and/or co-surfactant part of the system—all or part of the lipophilic component, i.e. the di- and triglyceride component, for the compositions of the present invention.

Still other commercial surfactant and/or co-surfactant compositions having significant di- and triglyceride content are known to those skilled in the art. It should be appreciated that such compositions, which contain di- and triglycerides as well as surfactants and/or co-surfactants, may be suitable to provide the complete system composed of surfactant, co-surfactant and lipophilic phase, of the compositions of the present invention. Typical examples for such kind of systems are so-called macrogolglycerides (or polyoxyethylated glycerides) with different kinds of fatty acids. Macrogolglycerides are mixtures of mono-esters, di-esters and tri-esters of glycerol and mono-ester and di-ester of PEG (=polyethylene glycol, macrogol, polyoxyethlene, polyethylene oxide, polyglycol) with fatty acids, whereby the molecular mass of the PEG may be defined as well as the nature of the fatty acids. Macrogolglycerides can be obtained by a partial hydrolyzis/esterification reaction of triglycerides using the respective macrogol. Alternatively, macrogolglycerides can be obtained by esterification of glycerol and the macrogol and the corresponding free fatty acids. As triglycerides a variety of natural and/or hydrogenated oils can be used. Most commonly used oils are castor oil or hydrogenated castor oil or an edible vegetable oil such as corn oil, olive oil, peanut oil, palm kernel oil, apricot kernel oil, or almond oil, or the corresponding hydrogenated vegetable oil.

Typically, such transesterification products of oils and polyethylenglycol (or other polyalcohols) are named by there educts: PEG-20 castor oil, PEG-23 castor oil, PEG-30 castor oil, PEG-35 castor oil, PEG-38 castor oil, PEG-40 castor oil, PEG-50 castor oil, PEG-56 castor oil, PEG-7 hydrogenated castor oil, PEG-10 hydrogenated castor oil, PEG-20 hydrogenated castor oil, PEG-25 hydrogenated castor oil, PEG-30 hydrogenated castor oil, PEG-40 hydrogenated castor oil, PEG-45 hydrogenated castor oil, PEG-50 hydrogenated castor oil, PEG-60 hydrogenated castor oil, PEG-80 hydrogenated castor oil, PEG-8 corn oil, PEG-20 corn oil, PEG-20 almond oil, PEG-25 trioleate, PEG-40 palm kernel oil, —PEG-60 corn oil, PEG-60 almond oil, PEG-8 caprylic/capric glycerides, lauroyl macrogol-32 glyceride (=PEG-32 hydrogenated palm kernel oil, e.g. Gelucire® 44/14), stearoyl macrogol glyceride (e.g. Gelucire® 50/13)

Examples of commercial co-surfactant compositions of mono-glycerides, in addition containing di- and triglycerides include some members of the co-surfactant families Maisines® (Gattefosse) and Imwitors® (Hüls). These commercial compositions may be used for providing the co-surfactant and the lipophilic phase in one composition. Specific examples of these compositions are: Maisine® 35-I (linoleic glycerides) and Imwitor® 742 (caprylic/capric glycerides).

"Aliphatic carboxylic acids with 6 to 22 carbon atoms": In the context of the present invention, aliphatic carboxylic acids with 6 to 22 carbon atoms are understood to be aliphatic $C_6$-$C_{22}$ carboxylic acids. Thus preferably carboxylic acids selected from the group containing caproic acid (C6), caprylic acid (C8), capric acid (C10), lauric acid (C12), myristic acid (C14), palmitic acid (C16), stearic acid (C18), arachidic acid (C20), and behenic acid (C22), as well as the corresponding unsaturated carboxylic acids, such as palmitoleic acid (C16), oleic acid (C18), linoleic acid (C18), linolenic acid (C18), eicosenoic acid (C20), individually or as a mixture, are used. Particularly preferably, the saturated carboxylic acids are selected.

"Aliphatic alcohols with 12 to 18 carbon atoms": In the context of the present invention, aliphatic alcohols with 12 to 18 carbon atoms are understood to be aliphatic $C_{12}$-$C_{18}$ alcohols. Preferably alcohols selected from the group consisting of lauryl alcohol (C12), myristyl alcohol (C14), cetyl alcohol (C16), stearyl alcohol (C18), oleyl alcohol (C18), linoleyl alcohol (C18) and linolenyl alcohol (C18), individually or as a mixture, are used. Particularly preferably, the saturated alcohols are selected.

"Aliphatic alcohols with 12 to 22 carbon atoms": In the context of the present invention, aliphatic alcohols with 12 to 22 carbon atoms are understood to be aliphatic $C_{12}$-$C_{22}$ alcohols. Preferably alcohols selected from the group consisting of lauryl alcohol (C12), myristyl alcohol (C14), cetyl alcohol (C16), stearyl alcohol (C18), arachidyl alcohol (C20), behenyl alcohol (C22), oleyl alcohol (C18), linoleyl alcohol (C18) and linolenyl alcohol (C18), individually or as a mixture, are used. Particularly preferably, the saturated alcohols are selected.

The "hydrophilic phase" in the context of the present invention is understood in particular to mean an aqueous phase which is preferably supplied by the physiological liquid of the digestion medium and/or by an aqueous liquid ingested in parallel with the food and/or the pharmaceutical preparation.

"Enzymes or enzyme mixtures with at least lipolytic activity" in the context of the present invention are understood to mean physiologically acceptable enzyme mixtures which contain at least one lipase. The enzymes or enzyme mixtures may, however, also have proteolytic activity in addition to the lipolytic activity, i.e. contain at least one protease, and/or amylolytic activity, i.e. contain at least one amylase.

Enzymes or enzyme mixtures may be used which exhibit (i) purely lipolytic; or (ii) lipolytic and proteolytic; or (iii) lipolytic and amylolytic; or (iv) lipolytic, proteolytic and amylolytic activity. Suitable enzymes or enzyme mixtures may be of any animal or microbiological origin. The enzyme mixtures with at least lipolytic, and optionally also proteolytic and/or amylolytic activity used in the context of the invention may therefore be of purely microbial origin or of purely animal origin, or alternatively represent a mixture of enzymes of animal and microbial origin.

Lipase-containing enzyme products of non-animal origin as well as preparations thereof, are enzyme mixtures comprising at least one lipase and optionally also at least one protease and/or amylase. These enzymes may be plant-derived or of fungal or bacterial origin. These lipases, proteases and/or amylases may, for example, be obtained by fermentation of optionally recombinant bacteria or fungi. The lipase-containing enzyme products may be composed of purely microbial derived enzyme preparations (i.e. enzymes obtained from fungi or bacteria) or enzyme preparations obtained from plants, but also of synthetic mixtures of enzyme preparations from plants, bacteria and/or fungi, optionally produced recombinantly in a microbial system. Furthermore, the recombinantly produced enzyme may be an enzyme variant or a mutated enzyme which is functionally equivalent or which has structural features similar to a naturally occurring enzyme.

By "recombinantly produced microbial enzyme", in particular "recombinantly produced lipase, amylase or protease", is meant an enzyme produced by recombinant DNA-technology, the enzyme being of microbial origin, i.e. obtained from fungi or bacteria. In the context of this invention suitable lipases include recombinantly produced microbial lipases that possess lipolytic activity, preferably at relatively low pH. In the context of this invention suitable proteases include recombinantly produced microbial proteases that possess proteolytic activity, preferably at relatively low pH. In the context of this invention suitable amylases include recombinantly produced microbial amylases that possess amylolytic activity, preferably at relatively low pH.

The recombinantly produced microbial enzyme, i.e. the lipase, amylase or protease, may be an enzyme variant or a mutated enzyme which is functionally equivalent or which has structural features similar to a naturally occurring enzyme.

Preferred recombinantly produced microbial lipases include lipases derived from fungi, e.g. from *Humicola, Rhizomucor, Rhizopus, Geotrichum* or *Candida* species, in particular *Humicola lanuginosa* (*Thermomyces lanuginosa*), *Rhizomucor miehei, Rhizopus javanicus, Rhizopus arrhizus, Rhizopus oryzae, Rhizopus delamar, Candida cylindracea, Candida rugosa* or *Geotrichum candidum*; or may be derived from bacteria, e.g. from *Pseudomonas, Burkholderia* or *Bacillus* species, in particular *Burkholderia cepacia*. Most preferred are lipases derived from a strain of *Humicola lanuginosa* (*Thermomyces lanuginosa*) or *Rhizomucor miehei*.

Lipases of microbial origin which can be used in the context of the present invention and their production by e.g. recombinant technology are described, for example, in U.S. Pat. No. 5,614,189 (=EP 600,868), U.S. Pat. No. 5,766,912 (=EP 238,023), U.S. Pat. No. 5,536,661 (=EP 305,216), U.S. Pat. No. 6,051,220 (=EP 828,509), U.S. Pat. No. 5,849,296 (=EP 550,450), U.S. Patent Publication No. 2001/046493 (=EP 1,261368), U.S. Pat. No. 6,140,475 (=EP 973,878) and U.S. Pat. No. 5,489,530 (=EP 592,478), which publications are each hereby incorporated by reference.

Preferred recombinantly produced microbial amylases include amylases derived from fungi, e.g. from *Aspergillus* or *Rhizopus* species, in particular *Aspergillus niger* or *Aspergillus oryzae*; or may be derived from bacteria, e.g. from *Bacillus* species, in particular *Bacillus subtilis*. Amylases derived from a strain of *Aspergillus oryzae* are most preferred.

Amylases of microbial origin which can be used in the context of the present invention and their production by recombinant technology are described in e.g. U.S. Pat. No. 6,051,220 (=EP 828,509) which publication is hereby incorporated by reference.

Preferred recombinantly produced microbial proteases include proteases derived from fungi, e.g. from *Aspergillus* or *Rhizopus* species, in particular *Aspergillus melleus, Aspergillus oryzae, Aspergillus niger*, or *Rhizopus oryzae*; or may be derived from bacteria, e.g. from *Bacillus* species, in particular *Bacillus subtilis*. Most preferred are proteases derived from a strain of *Aspergillus* melleus.

Proteases of microbial origin which can be used in the context of the present invention are described in e.g. U.S. Pat. No. 6,767,729 (=EP 1,186,658), which is hereby incorporated by reference, and in Pariza M. W. & Johnson E. A., "Evaluating the safety of microbial enzyme preparations used in food processing: update for a new century." *Regul Toxicol Pharmacol*. 2001 April; 33(2):173-86. (Review).

The recombinantly produced microbial enzyme, i.e. lipase, amylase or protease, preferably the recombinantly produced lipase, may be obtained by fermentation of a fungal cell, e.g. belonging to the genus *Aspergillus*, such as *A. niger, A. oryzae*, or *A. nidulans*; a yeast cell, e.g. belonging to a strain of *Saccharomyces*, such as *S. cerevisiae*, or a methylotrophic yeast from the genera *Hansenula*, such as *H. polymorpha*, or *Phichia*, such as *P. pastoris*; or a bacterial cell, e.g. belonging to a strain of *Bacillus*, such as *B. subtilis*, or *B. lentus*; the cell being transformed with the gene encoding the microbial lipase. Most preferred host organisms are members of *Aspergillus oryzae*.

An enzyme variant or mutated enzyme is obtainable by alteration of the DNA sequence of the parent gene or its derivatives. The enzyme variant or mutated enzyme may be expressed and produced when the DNA nucleotide sequence encoding the respective enzyme is inserted into a suitable vector in a suitable host organism. The host organism does not necessarily have to be identical to the organism from which the parent gene originated. The methods for introducing mutations into genes are well known in the art, see, for example, U.S. Pat. No. 5,658,871 (=EP 407, 225), the disclosure of which is incorporated by reference.

Preferred lipase variants or mutated lipases are obtainable from parent microbial lipases. In a preferred embodiment the parent lipase is derived from a fungus, e.g. a strain of *Humicola* or *Rhizomucor*, preferably a strain of *Humicola lanuginosa* or a strain of *Rhizomucor miehei*. In another preferred embodiment the parent lipase is derived from yeast, e.g. from a strain of *Candida*. In a further preferred embodiment the parent lipase is derived from a bacterium, e.g. from a strain of *Pseudomonas*. More preferred lipase variants or mutated lipases are lipase variants of parent lipases comprising a trypsin-like catalytic triad including an active serine residue located in a predominantly hydrophobic, elongated binding pocket of the lipase molecule, in which the electrostatic charge and/or hydrophobicity of a lipid contact zone comprising residues located in the vicinity of the lipase structure containing the active serine residue, which residues may participate in the interaction with the substrate at or during hydrolyzis, has been changed by deleting or substituting one or more negatively charged amino acid residues by neutral or positively charged amino acid residue(s), and/or by replacing one or more neutral amino acid residues with positively charged amino acid residue(s), and/or by deleting or substituting one or more hydrophobic amino acid residues by hydrophobic amino acid residue(s).

Pharmaceutically compatible auxiliaries, carriers and/or excipients useful in the context of the present invention are preferably selected from the group consisting of free polyethylene glycols having an average molecular weight of about 200 to about 6000; glycerol; lower alcohols, in particular straight-chain or branched $C_1$-$C_4$-alcohols such as 2-propanol; sugars, such as lactose, sucrose or dextrose; polysaccharides, such as maltodextrin or dextrates; starches; cellulosics, such as microcrystalline cellulose or microcrystalline cellulose/sodium carboxymethyl cellulose; inorganics, such as dicalcium phosphate, hydroxyapitite, tricalcium phosphate, talc, or titania; and polyols, such as mannitol, xylitol, sorbitol or cyclodextrin; and mixtures of the aforementioned substances.

The present invention includes pharmaceutical compositions for oral administration, which are self-emulsifiable on contact with a hydrophilic phase and a lipophilic phase, the compositions comprising:
  (i) enzymes or enzyme mixtures with at least lipolytic activity, and
  (ii) a system comprising
    at least one surfactant,
    at least one co-surfactant, and
    optionally a lipophilic phase.

Preferably the pharmaceutical composition according to the invention comprises enzymes or enzyme mixtures with at least lipolytic activity and a system comprising
  at least one surfactant having an HLB value above 6 and below 18,
  at least one co-surfactant having an HLB-value below 10, and a lipidic (lipophilic) phase,
  wherein the system comprising surfactant, co-surfactant and lipophilic phase has an HLB value of about 4 to 16, and a melting point of at least 20° C., preferably of at least 25° C.

The surfactant of the system is preferably selected from the group consisting of polyethylene glycol fatty acid esters; polyethylene glycol glycerol fatty acid esters; polyethylene glycol alkyl ethers, polyethylene glycol sterol ethers, polyethylene glycol sorbitan fatty acid esters, sugar esters, polyoxyethylene-polyoxypropylene block copolymers, ionic surfactants and mixtures thereof. Even more preferred, the surfactant is selected from the group consisting of polyethylene glycol (PEG) fatty acid mono- and/or di-esters with aliphatic $C_6$-$C_{22}$ carboxylic acids; polyethylene glycol (PEG) glycerol fatty acid esters with aliphatic $C_6$-$C_{22}$ carboxylic acids; polyethylene glycol (PEG) alkyl mono- and/or di-ethers with aliphatic $C_{12}$-$C_{18}$ alcohols, and mixtures thereof. In particular, the surfactant used is represented by a mixture of polyethylene glycol (PEG) mono- and di-esters with aliphatic $C_6$-$C_{22}$ carboxylic acids and/or polyethylene glycol (PEG) mono- and di-ethers with aliphatic $C_{12}$-$C_{18}$ alcohols, wherein the polyethylene glycol (PEG) comprises 6 to 60 ethylene oxide units per molecule (PEG-6 to PEG-60, also named as PEG 300 to PEG 3000). Preferably the surfactant is a mixture of polyethylene glycol mono- and di-esters with aliphatic $C_6$-$C_{22}$ carboxylic acids, wherein the polyethylene glycol comprises 6 to 40 ethylene oxide units per molecule.

The co-surfactant of the system is preferably selected from the group consisting of mono-acylglycerides, mono-ethers of glycerol, partial esters of propylenglycol, partial esters of polyglycerol, partial esters of ethyl diglycol and mixtures thereof. Even more preferred is a co-surfactant selected from the group consisting of mono-acylglycerides with aliphatic $C_6$-$C_{22}$ carboxylic acids, mono-ethers of glycerol ethers with aliphatic $C_{12}$-$C_{18}$ alcohols, partial esters of propylenglycol with aliphatic $C_6$-$C_{22}$ carboxylic acids, partial esters of polyglycerol with aliphatic $C_6$-$C_{22}$ carboxylic acids, and mixtures thereof. Particularly preferred co-surfactants are monoacylglycerides of aliphatic $C_6$-$C_{22}$ carboxylic acids and/or monoethers of glycerol with aliphatic $C_{12}$-$C_{22}$ alcohols, especially monoacylglycerides of aliphatic $C_6$-$C_{22}$ carboxylic acids.

The "lipophilic phase" is preferably represented by di- and/or triacylglycerides, especially preferably by di- and/or triacylglycerides with aliphatic $C_6$-$C_{22}$ carboxylic acids.

In one preferred embodiment, the system which is part of the pharmaceutical composition comprises
  as surfactant a mixture of polyethylene glycol (PEG) mono- and di-esters with aliphatic $C_6$-$C_{22}$ carboxylic acids and/or polyethylene glycol (PEG) mono- and di-ethers with aliphatic $C_{12}$-$C_{18}$ alcohols, in which the polyethylene glycol (PEG) comprises 6 to 60 ethylene oxide units per molecule, preferably a mixture of polyethylene glycol mono- and di-esters with aliphatic $C_6$-$C_{22}$ carboxylic acids, in which the polyethylene glycol comprises 6 to 40 ethylene oxide units per molecule;
  as co-surfactant monoacylglycerides of aliphatic $C_6$-$C_{22}$ carboxylic acids and/or monoethers of glycerol with aliphatic $C_{12}$-$C_{22}$ alcohols, preferably monoacylglycerides of aliphatic $C_6$-$C_{22}$ carboxylic acids, and
  as lipophilic phase di- and triacylglycerides of aliphatic $C_6$-$C_{22}$ carboxylic acids.

In the pharmaceutical composition according to the invention the system preferably comprises:
  2 to 90% by weight surfactants as defined above,
  5 to 60% by weight co-surfactants as defined above, and
  0 to 70% by weight of the lipophilic phase as defined above,
  in which the components surfactant, co-surfactant and the lipophilic phase together make up to 100% by weight of the system, and in which the system consisting of surfactant, co-surfactant and the lipophilic phase makes up 10% to 95% by weight of the pharmaceutical composition.

Preferably, the system consisting of surfactant, co-surfactant and lipophilic phase makes up 10 to 70% by weight, preferably 20 to 50% by weight, more preferably 25 to 40% by weight, of the pharmaceutical composition.

In a further embodiment of the pharmaceutical composition according to the invention, the system comprises:

40 to 90% by weight, preferably 60 to 85% by weight, surfactants, 5 to 40% by weight, preferably 15-30% by weight, co-surfactants, and 0 to 40% by weight, preferably 15-30% by weight, of the lipophilic phase, and the total of co-surfactants and the lipophilic phase together is at least 10% by weight, preferably between 15 and 40% by weight of the system.

In the context of the present invention, the pharmaceutical compositions may furthermore contain conventional pharmaceutically compatible auxiliaries, carriers and/or excipients as defined hereinafter.

In particular, the pharmaceutically compatible auxiliaries, carriers and/or excipients may be selected from the group consisting of free polyethylene glycols having an average molecular weight of about 200 to about 6000; glycerol; lower alcohols, in particular straight-chain or branched $C_1$-$C_4$-alcohols such as 2-propanol; sugars, such as lactose, sucrose or dextrose; cellulosics, such as microcrystalline cellulose or microcrystalline cellulose/sodium carboxymethyl cellulose; and mixtures of the aforementioned substances.

In a preferred embodiment, the proportion of the pharmaceutically compatible auxiliaries and/or excipients furthermore contained therein is at most 20% by weight of the pharmaceutical composition.

In a further preferred embodiment, the pharmaceutical composition according to the invention comprises a macrogolglyceride mixture representing the system consisting of surfactant, co-surfactant and lipophilic phase, in which the macrogolglycerides are a mixture of mono-, di- and tri-acylglycerides and polyethylene glycol (PEG) mono- and di-esters of aliphatic $C_6$-$C_{22}$ carboxylic acids, and optionally also small proportions of glycerol and free polyethylene glycol.

The polyethylene glycol (PEG) contained in the macrogolglyceride mixtures is preferably a PEG which has on average 6 to at most 40 ethylene oxide units per molecule or a molecular weight of between 200 and 2000.

One further aspect of the invention provides for the pharmaceutical composition to comprise a system consisting of surfactant, co-surfactant and lipophilic phase, the system having an HLB value of at least 10 and a melting point of at least 30° C. In a preferred embodiment, the system has an HLB value of 10 to 16, preferably of 12 to 15, and has a melting point of between 30 and 60° C., preferably between 40 and 50° C.

In particular, the system characterized by HLB value and melting point is a mixture of mono-, di- and triacylgylcerides and mono- and diesters of polyethylene glycol (PEG) with aliphatic carboxylic acids with 8 to 20 carbon atoms, in which the polyethylene glycol preferably contains about 6 to about 32 ethylene oxide units per molecule, and the system optionally contains free glycerin and/or free polyethylene glycol. The HLB value of such a system is preferably regulated by the chain length of the PEG. The melting point of such a system is regulated by the chain length of the fatty acids, the chain length of the PEG and the degree of saturation of the fatty-acid chains, and hence by the starting oil used for the preparation of the macrogolglyceride mixture.

The term "aliphatic $C_8$-$C_{18}$ carboxylic acids" designates mixtures in which caprylic acid (C8), capric acid (C10), lauric acid (C12), myristic acid (C14), palmitic acid (C16) and stearic acid (C18) are contained in a significant and variable proportion, if these acids are saturated, and the corresponding unsaturated $C_8$-$C_{18}$ carboxylic acids. The proportions of these fatty acids may vary depending on the starting oils.

Such a mixture of mono-, di- and triacylgylcerides and mono- and diesters of polyethylene glycol (PEG) with aliphatic carboxylic acids with 8 to 18 carbon atoms can, for example, be obtained by a reaction between a polyethylene glycol with a molecular weight of between 200 and 1500 and a starting oil, the starting oil consisting of a triglyceride mixture with fatty acids which are selected from the group consisting of caprylic acid, capric acid, lauric acid, myristic acid, palmitic acid, stearic acid, oleic acid and linolenic acid, individually or as a mixture. Optionally, the product of such a reaction may also contain small proportions of glycerin and free polyethylene glycol.

Such a mixture is commercially available, for example, under the trade name Gelucire®. One advantageous embodiment of the invention provides that, of the products known under the trade name Gelucire®, in particular "Gelucire® 50/13" and/or "Gelucire® 44/14" represent suitable mixtures for use in the pharmaceutical preparations according to the invention.

Gelucire® 50/13 is a mixture in which mono-, di- and triacylglycerides and mono- and diesters of polyethylene glycol, with palmitic acid (C16) and stearic acid (C18) at 40% to 50% and 48% to 58%, respectively, making up the major proportion of bound fatty acids. The proportion of caprylic acid (C8) and capric acid (C10) is less than 3% in each case, and the proportion of lauric acid (C12) and myristic acid (C14) in each case is less than 5%.

A preferred embodiment of the present invention provides a pharmaceutical composition which comprises a system containing a mixture of mono-, di- and triacylglycerides and polyethylene glycol mono- and diesters of aliphatic $C_8$-$C_{18}$ carboxylic acids and optionally also small proportions of glycerin and free polyethylene glycol, the system having a melting point between 46° C. and 51° C. and an HLB value of around 13.

Gelucire® 44/14 is a mixture of mono-, di- and triacylgylcerides and mono- and diesters of polyethylene glycol, the respective proportions of palmitic acid (C16) being 4 to 25%, stearic acid (C18) 5 to 35%, caprylic acid (C8) less than 15%, capric acid (C10) less than 12%, lauric acid (C12) 30 to 50% and myristic acid (C14) 5 to 25%. Gelucire® 44/14 can, for example, be prepared by an alcoholysis/esterification reaction using palm kernel oil and polyethylene glycol 1500.

One preferred embodiment of the present invention provides a pharmaceutical composition which comprises a system containing a mixture of mono-, di- and triacylglycerides and polyethylene glycol mono- and diesters of aliphatic $C_8$-$C_{18}$ carboxylic acids and optionally also small proportions of glycerin and free polyethylene glycol, the system having a melting point between 42° C. and 48° C. and an HLB value of around 14.

In an alternative embodiment of the pharmaceutical composition of the invention, an ionic surfactant is used as surfactant. Preferably, the ionic surfactant is selected from the group consisting of lecithin, lysolecithin, phosphatidylcholine, phosphatidylethanolamine, phosphatidylglycerol, phosphatidylserine, lysophosphatidylcholine, lysophosphatidylethanolamine, lysophosphatidylglycerol, lysophosphatidylinositol, lysophosphatidic acid, lysophosphatidylserine, and mixtures thereof. Lysophosphatidylcholine is especially preferred.

One particularly preferred pharmaceutical composition according to the invention comprises a system containing as surfactant lysophosphatidylcholine, as co-surfactant a mixture of mono-acylglycerides with aliphatic saturated and/or unsaturated $C_{16}$-$C_{20}$ carboxylic acids, preferably with oleic and/or linoleic acid, and a lipophilic phase of di- and/or triacylglycerides with aliphatic $C_{16}$-$C_{20}$ carboxylic acids, preferably with oleic and/or linoleic acid.

As a commercially available mixture of mono-, di- and triacylglycerides with aliphatic saturated and/or unsaturated $C_{16}$-$C_{20}$ carboxylic acids Maisine® (Gattefosse) can be used.

Preferably, the pharmaceutical composition is one in which the system comprises 2 to 10%, preferably about 5%, by weight lysophosphatidylcholine, 28 to 51% by weight mono-acylglycerides mainly of oleic acid and linoleic acid, and 36 to 54% by weight di-acylglycerides and 4 to 20% by weight tri-acylglycerides mainly of oleic acid and linoleic acid, in which the system consisting of surfactant, co-surfactant and the lipophilic phase together makes up 10% to 30%, preferably about 20%, by weight of the pharmaceutical composition.

For the pharmaceutical preparations according to the invention, preferably solid orally administered dosage forms may be selected, for example powders, pellets, granules, tablets, or microspheres, which if desired may be filled into capsules or sachets or may be compressed to form tablets. Granules are preferably produced by melt granulation. Tablets are usually made from a powder or from melt granules. Pellets can be produced either by exploiting the thermoplastic properties of the auxiliaries in a heavy-duty mixer (melt pelletization) or by traditional methods e.g. extrusion (e.g. melt extrusion or wet extrusion) and spheronisation. If individual enzyme types are present and are obtained separately, such as a lipase, a protease or an amylase from microbial origin, these may either be mixed together or spatially separated from each other. If the individual enzymes are not spatially separated from each other, dry processing and/or storage is preferred.

The pharmaceutical compositions according to the invention, which are self-emulsifiable on contact with a hydrophilic phase and optionally a lipophilic phase, contain enzymes or enzyme mixtures with at least lipolytic activity as active substance. In a preferred variant of the present invention, the enzymes or enzyme mixtures may however, in addition to the lipolytic activity, also have proteolytic activity, i.e. contain at least one protease, and/or amylolytic activity, i.e. contain at least one amylase.

In one preferred variant of the present invention, the lipolytic activity of the enzymes or enzyme mixtures is provided by a microbial lipase.

In another embodiment, the pharmaceutical composition contains enzymes or enzyme mixtures which comprise pancreatin and/or are pancreatin-like, preferably pancreatin-containing mixtures of digestive enzymes. Preferably, the pancreatin and/or pancreatin-like mixtures of digestive enzymes make up 65-85%, in particular 75-80%, by weight, of the pharmaceutical composition.

Alternatively, the enzyme mixture used is a mixture of at least one microbial lipase and one or more microbial enzymes selected from the group consisting of proteases and amylases.

In one variant of the invention, the enzyme mixture used is purely of microbial origin. Examples of such physiologically acceptable bacterial and/or fungal enzymes have already been described in the prior art, together with procedures for obtaining these enzymes and for their use in the treatment of maldigestion. For example, such synthetic mixtures of lipase, protease and amylase, each of which are microbially obtained, and also pharmaceutical preparations containing these mixtures are described in U.S. Patent Publication No. 2004/057944 (=WO 02/060474) and U.S. Pat. No. 6,051,220 (=EP 828,509).

Preferably, the pharmaceutical composition contains microbial enzymes making up 5-80%, in particular 20-60%, by weight of the pharmaceutical composition.

In the context of the invention, most preferred are those mixtures of digestive enzymes with lipolytic, proteolytic and amylolytic activity, the properties of which are close to those of pancreatin. Pancreatin-containing mixtures of digestive enzymes and also in particular pancreatin itself are therefore preferred in the context of the present invention as disclosed above. However it is possible, if desired, to add to the pancreatin or the pancreatin-containing mixtures of digestive enzymes one or more microbial enzymes, i.e. lipases, proteases and/or amylases obtained from microbial sources.

Suitable microbial enzymes for use as the sole enzyme mixture or as an addition to pancreatin or the pancreatin-containing mixtures of digestive enzymes include, in particular, bacterial or fungal enzymes, such as from the species *Bacillus* or *Pseudomonas*, or from fungal cultures, such as from the species *Aspergillus, Humicola* or *Rhizomucor*. Preferably, the microbial enzymes, in particular the microbial lipase, are recombinantly produced. In a further preferred variant of the present invention, the microbial lipase is a lipase variant or a mutated lipase.

The present invention furthermore relates to the use of a system comprising
　at least one surfactant,
　at least one co-surfactant, and
　optionally a lipophilic phase
for stabilizing the lipolytic activity in the acidic pH range and/or for improving the lipolytic activity of solid pharmaceutical preparations containing enzymes or enzyme mixtures with at least lipolytic activity, preferably pancreatin or pancreatin-like mixtures of digestive enzymes.

The possible further configurations of the system to be used, consisting of surfactant, co-surfactant and lipophilic phase, correspond to the embodiments described above for the self-emulsifiable pharmaceutical preparation according to the invention, which comprises such a system.

The invention also relates to a process for the preparation of solid pharmaceutical preparations containing enzymes or enzyme mixtures with at least lipolytic and optionally also proteolytic and/or amylolytic activity, preferably pancreatin and/or pancreatin-like mixtures of digestive enzymes. According to the invention, the enzymes or enzyme mixtures are converted into a suitable medicament form together with a system comprising
　a surfactant selected from the group consisting of polyethylene glycol fatty acid esters, polyethylene glycol glycerol fatty acid esters, polyethylene glycol alkyl ethers, polyethylene glycol sterol ethers, polyethylene glycol sorbitan fatty acid esters, sugar esters, polyoxyethylene-polyoxypropylene block copolymers, ionic surfactants, and mixtures thereof;
　a co-surfactant selected from the group consisting of mono-acylglycerides, mono-ethers of glycerol, partial esters of propylenglycol, partial esters of polyglycerol, partial esters of ethyl diglycol, and mixtures thereof, and
　a lipophilic phase, which is represented by di- and/or triacylglycerides,
and also optionally conventional, pharmaceutically compatible auxiliaries, carriers and/or excipients.

The further possible configurations of the system consisting of surfactant, co-surfactant and lipophilic phase used in the preparation process correspond to the embodiments described above for the self-emulsifiable pharmaceutical preparation according to the invention, which comprises such a system.

The following examples are intended to illustrate the invention in further detail without limiting its scope:

EXAMPLE 1

Preparation of Pancreatin-Containing Compositions According to the Invention and Comparison of the Lipolytic Activity of a Conventional Pancreatin Formulation and a Pancreatin Formulation According to the Invention Comprising a System Consisting of a Surfactant, Co-Surfactant and Lipophilic Phase a) Conventional Preparation (Pellets) NOT According to the Invention:

The conventional formulation was prepared according to the process disclosed in U.S. Pat. No. 5,378,462 (=EP 583, 726). 120 g pancreatin and 30 g PEG 4000 were initially dry-mixed and then moistened with 20 g isopropanol. The moist mixture was extruded and then rounded in a suitable rounder with the aid of paraffin oil. The resulting pellets were then dried.

b) Preparation According to the Invention (Pellets) (Example 1A)

350 g Gelucire® 50/13 was melted in a beaker in a water bath at a temperature of 52° C. The molten mass was mixed with 650 g pancreatin in a dual-jacket mixer for 10 min. The homogenous mixture was placed in a melt extruder for extrusion. Then the extrudate was rounded in a suitable rounder or spheroniser. The resulting pellets had a diameter of 1.0-1.6 mm.

c) Preparation According to the Invention (Granules) (Example 1B)

300 g Gelucire® 44/14 was melted in a beaker in a water bath at a temperature of 48° C. The molten mass was mixed with 700 g pancreatin in a dual-jacket mixer for approximately 15 minutes and then cooled (melt granulation).

The activity of the lipase as a function of the pH value and the time-dependent change in lipase activity were determined in accordance with the method of the "Federation Internationale Pharmaceutique/European Pharmacopeia" (abbreviated hereinafter as FIP/Ph.Eur.). In this standard analysis method, the hydrolytic activity of the lipase in the sample to be investigated is determined with the substrate olive oil. The free fatty acids cleaved off from the triglycerides of the olive oil are titrated with sodium hydroxide solution at a constant pH of 9.0. The lipase activity of the sample is determined by comparing the rate at which the sample hydrolyzes an olive oil emulsion with the rate at which a suspension of a standard pancreas reference powder hydrolyzes the same substrate under the same conditions.

The absolute and relative lipolytic activity of the conventional preparation and the preparation 1A according to the invention (pellets) determined in each case in accordance with FIP/Ph.Eur. are summarized in the following Table 1. The absolute and relative lipolytic activity of the conventional preparation and the preparation 1B according to the invention (granules) determined in each case in accordance with FIP/Ph.Eur. are summarized in the following Table 2:

TABLE 1

Absolute and relative lipolytic activity of the standard preparation and the preparation according to the invention (pellets with Gelucire ® 50/13)

| Sample | Lipase activity starting pancreatin [U/g] | Theoretically present lipase activity in the formulation [U/g] | Measured absolute lipase activity [U/g] | Relative lipase activity [%] |
|---|---|---|---|---|
| Example 1A: Pellets | 92620 | 60203 | 63173 | 104 |
| Conventional formulation | 92620 | 74096 | 69650 | 94 |

TABLE 2

Absolute and relative lipolytic activity of the standard preparation and the preparation according to the invention (granules with Gelucire ® 44/14)

| Sample | Lipase activity starting pancreatin [U/g] | Theoretically present lipase activity in the formulation [U/g] | Determined absolute lipase activity [U/g] | Relative lipase activity [%] |
|---|---|---|---|---|
| Example 1B: Granules | 84787 | 59351 | 67653 | 114 |
| Conventional formulation | 84132 | 67306 | 64950 | 97 |

It is apparent from the data that the addition of systems comprising at least one surfactant, at least one co-surfactant and a lipophilic phase to pharmaceutical preparations of enzymes and enzyme mixtures with at least lipolytic activity, preferably pancreatin and/or pancreatin-like mixtures of digestive enzymes, contributes to improved lipolytic activity compared with conventional formulations of pancreatin known in the prior art.

The absolute lipolytic activity of the respective pharmaceutical preparation determined in accordance with FIP/Ph.Eur. is expressed with reference to the total lipolytic activity theoretically present in the sample in the form of a relative activity, in order to take account of the different concentrations of pancreatin in the formulations. Comparison of the relative lipase activities determined shows that the relative lipase activity of the preparations according to the invention is approximately 10% higher than those of the conventional formulations. Accordingly, the pharmaceutical preparations according to the invention have increased lipolytic activity compared with conventional pancreatin formulations.

Furthermore, with reference to the value of the relative lipase activity of the preparation according to the invention of more than 100%, it is apparent that the system consisting of surfactant, co-surfactant and optionally lipophilic phase added to the preparations according to the invention exerts an activating effect on the lipase.

EXAMPLE 2

Comparison of the Stability of Lipolytic Activity of a Conventional Pancreatin Formulation and a Pancreatin Formulation According to the Invention Comprising a System Consisting of a Surfactant, Co-Surfactant and Lipophilic Phase at Different pH Values In order to compare the stability of lipolytic activity of a conventional pancreatin formulation and a pharmaceutical formulation according to the invention comprising an enzyme mixture with at least lipolytic activity and a system consisting of at least one surfactant, at least one co-surfactant, and a lipophilic phase, the activity of such a conventional pancreatin formulation was compared with the activity of a mixture of Gelucire® and pancreatin incubated for up to 2 hours at different pH values (pH 6, pH 5 and pH 4).

a) Standard Preparation (Pellets):

The conventional formulation was prepared according to the process disclosed in U.S. Pat. No. 5,378,462. 120 g pancreatin and 30 g PEG 4000 were initially dry-mixed and then moistened with 20 g isopropanol. The moist mixture was extruded and then rounded in a suitable rounder with the aid of paraffin oil. The resulting pellets were then dried.

b) Preparation According to the Invention (Pellets)—Example 2

300 g Gelucire® 44/14 was melted in a beaker in a water bath at a temperature of 48° C. The molten mass was mixed with 700 g pancreatin in a dual-jacket high-speed mixer (melt pelletization).

The activity of the lipase as a function of the pH value and also the time-dependent change in lipase activity were determined in accordance with the method of the FIP/Ph.Eur. as described above.

To determine the release behavior of the lipase in the conventional preparation and the preparation according to the invention at different pH values, the samples were incubated in a decomposition apparatus for 2 hours at 37° C. in phosphate buffer solution (pH 6, pH 5, pH 4). Samples were taken at intervals of 15 minutes, and the lipolytic activity in the samples was determined in accordance with the FIP/Ph.Eur. method described above.

600 ml buffer (67 mM phosphate, 34 mM NaCl, pH 6.0, pH 5.0, pH 4.0) was heated to a constant temperature of 37° C. in a 1 liter beaker in the decomposition tester. Once the constant temperature had been reached, 2 g of sample was added to the beaker and the decomposition tester was set in motion. The pH value of the phosphate buffer was kept constant during the testing time. Samples were taken at intervals of 15 minutes in each case, and the lipolytic activity in the samples was determined in accordance with FIP/Ph.Eur.

The relative lipolytic activities of the conventional preparation and the preparation according to the invention determined after 15, 30, 45, 60, 75, 90, 105 and 120 minutes in accordance with FIP/Ph.Eur. are summarised in the following Table 3. Details are given in % of the activity of the respective sample compared with a standard pancreas reference powder in accordance with FIP/Ph.Eur.

TABLE 3 pH-dependency of the relative lipolytic activity of a conventional pancreatin formulation and a pancreatin preparation according to the invention

| | pH 6 | | pH 5 | | pH 4 | |
|---|---|---|---|---|---|---|
| Time [min] | Conventional formulation | Example 2 | Conventional formulation | Example 2 | Conventional formulation | Example 2 |
| 15 | 93 | 98 | 89 | 100 | 30 | 55 |
| 30 | 90 | 101 | 82 | 99 | 19 | 39 |
| 45 | 84 | 97 | 77 | 95 | 13 | 31 |
| 60 | 81 | 89 | 72 | 95 | 11 | 27 |
| 75 | 79 | 82 | 71 | 94 | 8 | 23 |
| 90 | 76 | 76 | 68 | 92 | 7 | 19 |
| 105 | 72 | 71 | 65 | 89 | 6 | 18 |
| 120 | 69 | 66 | 61 | 86 | 5 | 17 |

It can be seen from this data that the addition of systems consisting of at least one surfactant, at least one co-surfactant, and a lipophilic phase to pharmaceutical preparations of enzymes and enzyme mixtures having at least lipolytic activity, preferably pancreatin and/or pancreatin-like mixtures of digestive enzymes, contributes to stabilizing the lipolytic activity in the acidic pH range. At a pH value of 6, comparison of the lipolytic activity of a conventional pancreatin preparation and a pancreatin preparation according to the invention over a time of 120 minutes shows that the lipolytic activity in both preparations over time decreases only relatively slightly, with the lipolytic activity of the preparation according to the invention increased by approximately 10% compared with the conventional formulation again being observed within the first hour. However, a pH value of 6 is known not to have any great influence on the lipolytic activity. On the other hand, at a pH value of 5 the lipolytic activity of the conventional preparation decreases much more quickly compared with the preparation according to the invention. Whereas the preparation according to the invention has lost less than 10% of the lipolytic activity after 90 minutes, the conventional preparation has only a lipolytic activity of less than 70% remaining compared with a pancreas reference powder in accordance with FIP/Ph.Eur. In particular at a pH value of 4, the preparation according to the invention has a markedly greater lipolytic (residual) activity than the conventional preparation. Accordingly, it can be seen that the pharmaceutical preparations according to the invention have a substantially increased lipolytic activity in an acidic pH medium.

EXAMPLE 3

Dosage Dependence of a Pancreatin Formulation According to the Invention Comprising a System Consisting of a Surfactant, co-Surfactant and Lipophilic Phase on Digestibility of a High Fat Diet in the Pancreatic Exocrine Deficient Minipig The efficacy of a pelleted pharmaceutical formulation according to the invention comprising an enzyme mixture with at least lipolytic activity and a system consisting of at least one surfactant, at least one co-surfactant, and a lipophilic phase to improve digestion and absorption of fat in minipigs, in which the pancreatic duct has been ligated to induce a complete pancreatic exocrine insufficiency, was analyzed in pigs fed a high (32%) fat diet.

a) Preparation According to the Invention (Pellets)

250 g Gelucire® 44/14 (Gattefossé) was melted in a beaker in a water bath at a temperature of 48° C. The molten mass was mixed with 750 g pancreatin in a dual-jacket high-speed mixer (melt pelletization). The pellet size of this formulation was similar to that of the commercially available pancreatin product.

Determination of the Activity of Lipase

Studies were performed in 6 minipigs (Ellegaard, female Göttingen minipigs) with induced pancreatic exocrine insufficiency, weighing 20-30 kg at surgery. The pigs were prepared as previously described by Tabeling R., Gregory P., Kamphues J., 1999: Studies on nutrient digestibilities (precaecal and total) in pancreatic duct-ligated pigs and the effects of enzyme substitution. *J. Anim. Physiol. a. Anim. Nutr.* 82, 251-263. The pancreatic duct was ligated under halothane anaesthesia following a mid-line laparotomy; after which the pigs were chronically fitted with an ileo-caecal re-entrant fistula which was exteriorized on the right flank.

The success of the pancreatic duct ligation was confirmed by a faecal chymotrypsin test before starting the digestibility studies, which began at least 4 weeks after the pigs had recovered from the surgery.

The pigs were fed two 250 g meals/day (08.00 and 20.00 h) of a high fat diet (containing: 180 g double-milled Altromin 9021 [modified], 70 g soya oil [Roth]; overall contents are 99% dry matter, 4% crude ash, 32% crude fat, 16% crude protein, 28% starch, 3% crude fiber) plus 0.625 g $Cr_2O_3$ per meal, mixed with 1 liter water. The meals plus enzymes were carefully mixed together immediately before offering to the pigs. The meals were generally consumed within 5 minutes.

During the study the pigs received zero, 28,000 or 336,000 FIP lipase units per meal as a formulation according to the invention for 14 days, with a complete collection of faeces for the last 5 days. The faeces (and the feed) were frozen at −20° C., freeze dried, and a Weender analysis was performed [Naumann C, Bassler R. 1993: Die chemische Untersuchung von Futtermitteln. 3. Aufl. VDLUFA-Verlag, Darmstadt] to determine content of dry matter (drying at 103° C. for 8 hours), and crude fat (determined gravimetrically after boiling for 30 minutes with conc. HCl, followed by a 6 hours extraction with petroleum ether). $Cr_2O_3$ was oxidized to chromate, and chromium content was calculated via extinction at 365 nm [Petry H, Rapp W. 1970: Zur Problematik der Chromoxidbestimmung in Verdauungsversuchen. *Z. Tierphysiol. Tierernährung und Futtermitellkunde* 27, 181-189].

Based on the content of fat and chromium determined per 100 g dry matter feed and faeces (see above), the digestibility of fat (CFA) was calculated according to the formula:

$$\% \text{ fat digestibility} = 100 - \left( \frac{[\% \text{ } Cr_2O_3 \text{ in feed}]}{[\% \text{ } Cr_2O_3 \text{ in faeces}]} \times \frac{[\% \text{ fat in faeces}]}{[\% \text{ fat in feed}]} \times 100 \right)$$

The efficacy to improve digestion and absorption of fat in minipigs, in which the pancreatic duct has been ligated to induce a complete pancreatic exocrine insufficiency, measured in the % fat digestibility is given for the preparation according to the invention for different amounts of lipase activity added (given in FIP/Ph.Eur. units).

TABLE 4

% fat digestibility in minipigs receiving a pancreatin preparation according to the invention

| Substitution | 0 Lipase Units | 28,000 FIP lipase U/meal | 336,000 FIP lipase U/meal |
|---|---|---|---|
| No enzymes added | 31.66 ± 13.78 | | |
| Formulation according to the invention | | 61.98 ± 11.60 * | 79.25 ± 7.00 ** |

\*: ** Results are mean ± S.D.

It can be seen that the formulation according to the invention caused a very strong and dose-dependent improvement in fat digestibility, already showing a highly efficient improvement at the lower dose tested.

EXAMPLE 4

Comparison of the Stability of Lipolytic Activity of a Conventional Pancreatin Powder and a Pancreatin Formulation According to the Invention Comprising a System Consisting of a Surfactant, co-Surfactant and Lipophilic Phase at Different pH Values Further preparations according to the invention were prepared and analyzed with regard to their lipolytic activity in comparison to pancreatin powder at different acidic pH values (pH 6, pH 5 and pH 4).

a) Preparation for Comparison Not According to the Invention:

Pancreatin powder b) Preparation According to the Invention—Example 4A 700 g Pancreatin powder 200 g Gelucire™ 44/14 (Gattefosse)

100 g Labrasol™ (Gattefosse)

The Gelucire® 44/14 and the Labrasol® were mixed and melted in a beaker in a water bath at a temperature of 48° C. The molten mass was mixed with 700 g pancreatin in a dual-jacket high-speed mixer (melt granulation).

c) Preparation According to the Invention—Example 4B 800 g Pancreatin powder 190 g Maisine® (Gattefosse)

10 g LPC (Lysophosphatidylcholine)

The Maisine® and the Lysophosphatidylcholine were mixed and melted in a beaker in a water bath at a temperature of 48° C. The molten mass was mixed with 800 g pancreatin in a dual-jacket high-speed mixer (melt granulation).

The activity of the lipase as a function of the pH value and also the time-dependent change in lipase activity were determined as described in Example 2.

The release behavior of the lipase at different pH values in the pancreatin powder and the preparation according to the invention was measured as described above for Example 2.

The relative lipolytic activity determined after 15, 30, 45, 60, 75, 90, 105 and 120 minutes of the pancreatin powder and the preparations "Example 4A" and "Example 4B" according to the invention in accordance with FIP/Ph.Eur. are summarized in the following Tables 5A and 5B. Details are given in % of the activity of the respective sample compared with a standard pancreas reference powder in accordance with FIP/Ph.Eur.

TABLE 5A pH-dependency of the relative lipolytic activity of a standard pancreatin powder and the pancreatin preparation "4A" according to the invention

| | pH | | | | | |
|---|---|---|---|---|---|---|
| | 6 | | 5 | | 4 | |
| Time [min] | Pancreatin Powder | Example 4A | Pancreatin Powder | Example 4A | Pancreatin Powder | Example 4A |
| 15 | 55.7 | 90.4 | 61.5 | 93.8 | 19.3 | 49.0 |
| 30 | 54.9 | 105.1 | 53.3 | 99.0 | 12.5 | 32.4 |
| 45 | 48.3 | 102.9 | 51.8 | 95.8 | 8.4 | 25.5 |
| 60 | 43.1 | 97.6 | 48.1 | 92.7 | 6.5 | 23.1 |
| 75 | 39.0 | 91.7 | 41.4 | 93.2 | 5.6 | 19.9 |
| 90 | 35.4 | 87.2 | 39.9 | 91.2 | 4.3 | 18.8 |
| 105 | 33.0 | 82.3 | 44.8 | 88.1 | 3.9 | 17.8 |
| 120 | 30.4 | 79.2 | 39.1 | 85.6 | 3.6 | 16.5 |

TABLE 5B pH-dependency of the relative lipolytic activity of a standard pancreatin powder and the pancreatin preparation "4B" according to the invention

| | pH | | | | | |
|---|---|---|---|---|---|---|
| | 6 | | 5 | | 4 | |
| Time [min] | Pancreatin Powder | Example 4B | Pancreatin Powder | Example 4B | Pancreatin Powder | Example 4B |
| 15 | 55.7 | 91.9 | 61.5 | 83.2 | 19.3 | 27.1 |
| 30 | 54.9 | 87.4 | 53.3 | 88.0 | 12.5 | 16.4 |
| 45 | 48.3 | 81.2 | 51.8 | 86.3 | 8.4 | 13.0 |
| 60 | 43.1 | 73.7 | 48.1 | 83.5 | 6.5 | 9.9 |
| 75 | 39.0 | 69.8 | 41.4 | 83.8 | 5.6 | 8.9 |
| 90 | 35.4 | 63.8 | 39.9 | 80.0 | 4.3 | 7.8 |
| 105 | 33 | 57.1 | 44.8 | 78.4 | 3.9 | 6.5 |
| 120 | 30.4 | 53.0 | 39.1 | 74.0 | 3.6 | 4.9 |

From these data it can be concluded that the addition of systems consisting of at least one surfactant, at least one co-surfactant, and a lipophilic phase to pharmaceutical preparations of enzymes and enzyme mixtures with at least lipolytic activity, preferably pancreatin and/or pancreatin-like mixtures of digestive enzymes, contributes to stabilizing the lipolytic activity in the acidic pH range.

EXAMPLE 5

Determination of the Lipolytic Activity of a Formulation According to the Invention Comprising a Lipase of Microbial Origin and a System Consisting of a Surfactant, Co-Surfactant and Lipophilic Phase and Determination of Stability at Different pH Values In order to determine the lipolytic activity and to show the improved stability at acidic pH of a pharmaceutical formulation according to the invention comprising an enzyme mixture with at least lipolytic activity, in which the lipolytic activity is provided by a microbial, optionally recombinantly produced lipase, and a system consisting of at least one surfactant, at least one co-surfactant, and a lipophilic phase, the activity of a pharmaceutical formulation consisting of a mixture of Gelucire™ and a microbial lipase is determined at different pH values (pH 6, pH 5, pH 4 and 3) and compared to a lipase preparation which has not been stabilized.

a) Preparation According to the Invention (Granulate)

562.5 g Gelucire® 44/14 was melted in a beaker in a water bath at a temperature of 48° C. 937.5 g of a microbial lipase preparation (the active lipase protein representing about 50 to 60% (w/w) of the dry matter of the preparation) were provided in a dual-jacket mixer at 46° C., then the molten Gelucire was added and the compounds were mixed, first at low speed for 3 min, then for approx. 15 min. at high speed, and finally cooled (melt granulation).

b) Comparison Preparation (Not According to the Invention)

A microbial lipase preparation was prepared by using common spray dry technique.

The activity of the lipase was determined in accordance with the method of the "Federation Internationale Pharmaceutique" (abbreviated hereafter to FIP) for microbial lipases, except that the concentration of bile salts is 10 mM.

Using this standard analysis method, the hydrolytic activity of the lipase in the sample to be investigated is determined using olive oil as a substrate. Released free fatty acids are titrated with sodium hydroxide solution at a constant pH of 7.0. The lipase activity of the sample is determined by comparison of the rate at which the sample hydrolyzes an olive oil emulsion with the rate at which a suspension of a microbial lipase reference powder hydrolyzes the same substrate under the same conditions.

To determine the pH-stability of the lipase at different pH values in an unstabilized preparation and in the preparation according to the invention, the samples were incubated in a decomposition apparatus for 2 hours at 37° C. in buffer solution (pH 5, pH 4 and pH 3). Samples were taken at intervals of 15 minutes, and the lipolytic activity in the samples was determined in accordance with the FIP method.

100 mg of lipase were incubated in 100 ml buffer (0.1 M malonic acid buffer, 1 mM calcium chloride pH 3, 4 and 5) at 37° C. Samples were drawn every 15 min for a total duration of 2 hours and the lipolytic activity of the samples was determined as follows: An olive oil suspension was prepared by mixing 175 g olive oil with 630 ml of a solution of 700 g of gum arabic and 94.4 g calcium chloride di-hydrate in 5,900 ml water for 15 minutes in a food mixer at maximal speed. The emulsion was cooled to 37° C., and the pH was adjusted to pH 6.8 with sodium hydroxide solution. Three reference solutions were prepared by extracting an appropriate amount of FIP microbial lipase standard with an ice-cold 1% (m/v) solution of sodium chloride such that reference solutions with 50 FIP-U/ml, 65 FIP-U/ml and 80 FIP-U/ml were obtained. Sample solutions were prepared by extracting an amount of sample corresponding to app. 6,500 units activity for 15 minutes with a total of 100 ml ice-cold 1% (m/v) solution of sodium chloride. The samples were further diluted in ice-cold 1% (m/v) solution of sodium chloride such that the titration rate was within the range of the titration rates obtained with the reference solutions.

The titration rates of the reference and sample solutions were determined by combining in a thermostated vessel 19 ml of olive oil suspension with 10 ml of a solution of 492 mg lipase activating mixture (FIP) in 500 ml of water. The combined solutions were thermostated to 37° C., and the pH was adjusted to pH 7.0. One ml of reference solution or sample solution were added, and the released fatty acids titrated under pH stable conditions with 0.1 M sodium hydroxide solution for a duration of 5 minutes. The titration rate was calculated by linear regression from at least 9 measurement points between the 60th and the 300th second of titration.

From the titration rates of the reference solutions a calibration function was calculated by linear regression. The calibration function takes the form $y=mx+b$ where y: titration rate; m: slope; x: FIP-units of the reference solution; and b: axis intercept. Using the values thus determined for m and b, the lipolytic activity x was calculated for each sample solution using the formula x=(y−b)/m.

The relative lipolytic activities determined after 0, 15, 30, 45, 60, 75, 90, 105 and 120 minutes of an un-stabilized microbial lipase preparation and the preparation according to the invention in accordance with FIP are determined. A comparison of the results obtained can show the improved lipolytic activity and the increased stability within the acidic pH range of the formulation according to the invention comprising a microbial lipase preparation over the un-stabilized lipase preparation.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A pharmaceutical composition for oral administration as a solid dosage form, comprising an active pharmaceutical agent and a surfactant system, which is self-emulsifiable on contact with a hydrophilic phase and a lipophilic phase, said composition comprising:
   (i) an active pharmaceutical agent which
      (a) is an enzyme or an enzyme mixture with at least lipolytic activity which exerts its action in the gastrointestinal tract, and
      (b) is admixed with a surfactant system to form the pharmaceutical composition wherein the pharmaceutical composition does not contain an enteric coating and does not contain any lipophilic active substances to be absorbed into the bloodstream; and
   (ii) wherein the surfactant system comprises
      a. a surfactant in an amount of 2% to 90% by weight of the surfactant system selected from either a first group or an ionic surfactant, wherein the first group consists of: polyethylene glycol fatty acid mono-esters and/or di-esters with aliphatic $C_6$-$C_{22}$ carboxylic acids; polyethylene glycol glycerol fatty acid esters with aliphatic $C_6$-$C_{22}$ carboxylic acids; polyethylene glycol alkyl mono-ethers and/or di-ethers with aliphatic $C_{12}$-$C_{18}$ alcohols, and mixtures of the foregoing; and wherein the ionic surfactant is selected from the group consisting of: lecithin, lysolecithin, phosphatidylcholine, phosphatidylethanolamine, phosphatidylglycerol, phosphatidylserine, lysophosphatidylcholine, lysophosphatidylethanolamine, lysophosphatidylglycerol, lysophosphatidylinositol, lysophosphatidic acid, lysophosphatidylserine, and mixtures of the foregoing;
      b. a co-surfactant in an amount of 5% to 60% by weight of the surfactant system, selected from a group consisting of monoacylglycerides with aliphatic $C_6$-$C_{22}$ carboxylic acids, monoethers of glycerol ethers with aliphatic $C_{12}$-$C_{18}$ alcohols, partial esters of propylenglycol with aliphatic $C_6$-$C_{22}$ carboxylic acids, partial esters of polyglycerol with aliphatic $C_6$-$C_{22}$ carboxylic acids, and mixtures of the foregoing; and
      c. a lipophilic phase in an amount of 0% to 70% by weight of the surfactant system, represented by diacylglycerides and/or triacylglycerides with aliphatic $C_6$-$C_{22}$ carboxylic acids;
   wherein the surfactant system comprises 10% to 95% by weight of the pharmaceutical composition.

2. A pharmaceutical composition according to claim 1, wherein the hydrophilic phase used to form the final emulsion after ingestion is supplied by the physiological fluid of the digestive milieu.

3. A pharmaceutical composition according to claim 1, wherein the lipophilic phase used to form the final emulsion in the digestive tract after ingestion is at least partially supplied by the lipids present in ingested food.

4. A pharmaceutical composition according to claim 1, wherein the surfactant system comprises as the lipophilic phase a lipidic phase, said surfactant system comprising surfactant, co-surfactant and lipophilic phase having a hydrophilic-lipophilic balance value of about 4 to 16, and a melting point of at least 20° C.

5. A pharmaceutical composition according to claim 4, wherein said surfactant system has a melting point of at least 25° C.

6. A pharmaceutical composition according to claim 1,
   a. wherein the surfactant is a mixture of polyethylene glycol mono-esters and di-esters with aliphatic $C_6$-$C_{22}$ carboxylic acids and/or polyethylene glycol mono-ethers and di-ethers with aliphatic $C_{12}$-$C_{18}$ alcohols, whereby the polyethylene glycol comprises 6 to 60 ethylene oxide units per molecule,
   b. wherein the co-surfactant is monoacylglycerides of aliphatic $C_6$-$C_{22}$ carboxylic acids and/or monoethers of glycerol with aliphatic $C_1$-$C_{22}$ alcohols, and
   c. wherein the lipophilic phase is diacylglycerides and triacylglycerides of aliphatic $C_6$-$C_{22}$ carobxylic acids.

7. A pharmaceutical composition according to claim 6, wherein the surfactant is a mixture of polyethylene glycol mono-esters and di-esters with aliphatic $C_6$-$C_{22}$ carboxylic acids, wherein the polyethylene glycol comprises 6 to 40 ethylene oxide units per molecule, and wherein the co-surfactant is monoacylglycerides of aliphatic $C_6$-$C_{22}$ carboxylic.

8. A pharmaceutical composition according to claim 1, wherein the surfactant system comprises 10% to 70% by weight of the pharmaceutical composition.

9. A pharmaceutical composition according to claim 8, wherein the surfactant system comprises 20% to 50% by weight of the pharmaceutical composition.

10. A pharmaceutical composition according to claim 9, wherein the surfactant system comprises 25% to 40% by weight of the pharmaceutical composition.

11. A pharmaceutical composition according to claim 1, wherein the surfactant system comprises:
   a. 40% to 90% by weight surfactants,
   b. 5% to 40% by weight co-surfactants, and
   c. 0% to 40% by weight of the lipophilic phase,
wherein the total of co-surfactants and the lipophilic phase together are greater than 10% by weight of the surfactant system.

12. A pharmaceutical composition according to claim 1, wherein the surfactant system comprises
   a. 60% to 85% by weight surfactants,
   b. 15% to 30% by weight co-surfactants, and
   c. less than 30% by weight of the lipophilic phase,
wherein the total of co-surfactants and the lipophilic phase together are between 15% and 40% by weight of the surfactant system.

13. A pharmaceutical composition according to claim 1, wherein the surfactant system comprises a lipophilic phase and further comprises a pharmaceutically compatible auxiliary, carrier or excipient selected from the group consisting of polyethylene glycol, glycerol, $C_1$-$C_4$ alcohols, sugars, cellulosics and mixtures thereof.

14. A pharmaceutical composition according to claim 13, wherein the pharmaceutically compatible auxiliary, carrier, or excipient is less than 20% by weight of the composition.

15. A pharmaceutical composition according to claim 1, wherein the surfactant system comprises a lipophilic phase and further comprises macrogolglycerides and optionally glycerin and/or free polyethylene glycol, wherein the macrogolglycerides are a mixture of (i) monoacylglyerides, diacylglycerides and triacylglycerides and (ii) polyethylene glycol monoesters and diesters of aliphatic $C_6$-$C_{22}$ carboxylic acids, wherein the polyethylene glycol comprising about 6 to about 32 ethylene oxide units per molecule.

16. A pharmaceutical composition according to claim 15, wherein the surfactant system has a hydrophilic-liopohilic balance value of greater than 10, and a melting point of greater than 30° C.

17. A pharmaceutical composition according to claim 16, wherein the surfactant system has a hydrophilic-lipophilic balance of 10 to 16, and a melting point of between 30° C. and 60° C.

18. A pharmaceutical composition according to claim 17, wherein the surfactant system has a hydrophilic-lipophilic balance of 12 to 15, and a melting point of between 40° C. and 50° C.

19. A pharmaceutical composition according to claim 17, wherein the surfactant system comprises a mixture of (i) monoacylglycerides, diacylglycerides and triacylglycerids, (ii) polyethylene glycol mono-esters and di-esters of aliphatic $C_8$-$C_{18}$ carobxylic acids, and (iii) optionally glycerol and/or free polyethylene glycol, and wherein the surfactant system has a melting point between 42° C. and 48° C. and a HLB of 14.

20. A pharmaceutical composition according to claim 17, wherein the surfactant system comprises a mixture of (i) monoacylglycerides, diacylglycerides and triacylglycerides, (ii) polyethylene glycol mono-esters and di-esters of aliphatic $C_8$-$C_{18}$ carboxylic acids and (iii) optionally glycerol and/or free polyethylene glycol, wherein the surfactant system has a melting point between 46° C. and 51° C. and an HLB value of 13.

21. A pharmaceutical composition according to claim 15, wherein the surfactant system comprises a mixture of (i) monoacylglycerides, diacylglycerides and triacylglycerides and polyethylene glycol PEG-32 mono-esters and di-esters mainly of aliphatic $C_8$-$C_{16}$ carboxylic acids, (ii) a mixture of monoacylglycerides, diacylglycerides and triacylglycerides and polyethylene glycol PEG-8 mono-esters and di-esters mainly of aliphatic $C_6$-$C_{10}$ carboxylic acids and (iii) optionally glycerol and/or free polyethylene glycol.

22. A pharmaceutical composition according to claim 1, wherein the surfactant is lysophosphatidylcholine, wherein the co-surfactant is a mixture of monoacylglycerides with aliphatic saturated and/or unsaturated $C_{16}$-$C_{20}$ carboxylic acids, and wherein the lipophilic phase is diacylglycerides and/or triacylglycerides with aliphatic $C_{16}$-$C_{20}$ carboxylic acids.

23. A pharmaceutical composition according to claim 22, wherein the co-surfactant is a mixture of monoacylglycerides with oleic and/or linoleic acid, and the lipophilic phase is diacylglycerides and/or triacylglycerides with oleic and/or linoleic acid.

24. A pharmaceutical composition according to claim 22, wherein the surfactant system comprises 2% to 10% by weight lysophosphatidylcholine, 28% to 51% by weight monoacylglycerides comprising oleic acid and linoleic acid, and 36% to 54% by weight diacylglycerides and 4% to 20% by weight triacylglycerides comprising oleic acid and linoleic acid, wherein the surfactant system comprises 10% to 30% by weight of the pharmaceutical composition.

25. A pharmaceutical composition according to claim 24, wherein the surfactant system comprises 5% by weight lysophosphatidylcholine, 28% to 51% by weight monoacylglycerides comprising oleic acid and linoleic acid, and % to 54% by weight diacylglycerides and 4% to 20% by weight triacylglycerides comprising oleic acid and linoleic cid, wherein the surfactant system is less than 20% by weight of the pharmaceutical composition.

26. A pharmaceutical composition according to claim 1, wherein the composition is a solid pharmaceutical preparation in the form of a powder, granules, tablets, or pellets.

27. A pharmaceutical composition according to claim 1, wherein the enzyme or enzyme mixture having lipolytic activity is bacterial or fungal in origin.

28. A pharmaceutical composition according to claim 1, wherein the enzymes or enzyme mixture also has proteolytic and/or amylolytic activity.

29. A pharmaceutical composition according to claim 1 wherein the enzyme or enzyme mixture having lipoltyic activity comprises pancreatin.

30. A pharmaceutical composition according to claim 29, wherein the pancreatin comprises 65% to 85% by weight of the pharmaceutical composition.

31. A pharmaceutical composition according to claim 30, wherein the pancreatin comprises 75% to 80% by weight of the pharmaceutical composition.

32. A pharmaceutical composition according to claim 28, wherein the enzyme or enzyme mixture comprises a mixture of at least one microbial enzyme selected from the group consisting of proteases and amylases.

33. A pharmaceutical composition according to claim 32, wherein microbial enzymes comprise 5% to about 80% by weight of the pharmaceutical composition.

34. A pharmaceutical composition according to claim 33, wherein microbial enzymes comprise 20% to 60% by weight of the pharmaceutical composition.

35. A pharmaceutical composition according to claim 1, wherein the enzyme or enzyme mixture further comprises at least one digestive enzyme selected from the group consisting of lipases, proteases and amylases.

36. A pharmaceutical composition according to claim 1, wherein the lipolytic activity results from microbial lipase which is a recombinantly produced fungal or bacterial lipase.

37. A pharmaceutical composition according to claim 36, wherein the microbial lipase is a lipase variant or a mutated lipase.

38. A method of orally administering a pharmaceutical composition as a solid oral dosage form which is self-emulsifying on contact with a hydrophilic phase and a lipophilic phase comprising the step of: orally administering a pharmaceutical composition comprising:
  (i) an active pharmaceutical agent which
    (a) is an enzyme or an enzyme mixture with at least lipolytic activity which exerts its action in the gastrointestinal tract, and
    (b) is admixed with a surfactant system to form the pharmaceutical composition wherein the pharmaceutical composition does not contain an enteric coating and does not contain any lipophilic active substances to be absorbed into the bloodstream; and
  (ii) wherein the surfactant system comprises
    a. a surfactant in an amount of 2% to 90% by weight of the surfactant system selected from either a first group or an ionic surfactant, wherein the first group consists of: polyethylene glycol fatty acid mono-esters and/or diesters with aliphatic $C_6$-$C_{22}$ carboxylic acids; polyethylene glycol glycerol fatty acid esters with aliphatic $C_6$-$C_{22}$ carboxylic acids; polyethylene glycol alkyl mono-ethers and/or di-ethers with aliphatic $C_{12}$-$C_{18}$ alcohols, and mixtures of the foregoing; and wherein the ionic surfactant is selected from the group consisting of: lecithin, lysolecithin, phosphatidylcholine, phosphatidylethanolamine, phosphatidylglycerol, phosphatidylserine, lysophosphatidylcholine, lysophosphatidylethanolamine, lysophosphatidylglycerol, lysophosphatidylinositol, lysophosphatidic acid, lysophosphatidylserine, and mixtures of the foregoing;

b. a co-surfactant in an amount of 5% to 60% by weight of the surfactant system, selected from a group consisting of monoacylglycerides with aliphatic $C_6$-$C_{22}$ carboxylic acids, monoethers of glycerol ethers with aliphatic $C_{12}$-$C_{18}$ alcohols, partial esters of propylenglycol with aliphatic $C_6$-$C_{22}$ carboxylic acids, partial esters of polyglycerol with aliphatic $C_6$-$C_{22}$ carboxylic acids, and mixtures of the foregoing; and c. a lipophilic phase in an amount of 0% to 70% by weight of the surfactant system, represented by diacylglyerides and/or triacylglycerides with aliphatic $C_6$-$C_{22}$ carboxylic acids;

wherein the surfactant system comprises 10% to 95% by weight of the pharmaceutical composition.

39. A pharmaceutical composition prepared by a process comprising the step of: combining
(i) an active pharmaceutical agent which
(a) is an enzyme or an enzyme mixture with at least lipolytic activity which exerts its action in the gastrointestinal tract,
(b) with a surfactant system to form the pharmaceutical composition wherein the pharmaceutical composition does not contain an enteric coating and does not contain any lipophilic active substances to be absorbed into the bloodstream; and
(ii) wherein the surfactant system comprises a. a surfactant in an amount of 2% to 90% by weight of the surfactant system selected from either a first group or an ionic surfactant, wherein the first group consists of: polyethylene glycol fatty acid mono-esters and/or di-esters with aliphatic $C_6$-$C_{22}$ carboxylic acids; polyethylene glycol glycerol fatty acid esters with aliphatic $C_6$-$C_{22}$ carboxylic acids; polyethylene glycol alkyl mono-ethers and/or di-ethers with aliphatic $C_{12}$-$C_{18}$ alcohols, and mixtures of the foregoing; and wherein the ionic surfactant is selected from the group consisting of: lecithin, lysolecithin, phosphatidylcholine, phosphatidylethanolamine, phosphatidylglycerol, phosphatidylserine, lysophosphatidylcholine, lysophosphatidylethanolamine, lysophosphatidylglycerol, lysophosphatidylinositol, lysophosphatidic acid, lysophosphatidylserine, and mixtures of the foregoing;

b. a co-surfactant in an amount of 5% to 60% by weight of the surfactant system, selected from a group consisting of monoacylglycerides with aliphatic $C_6$-$C_{22}$ carboxylic acids, monoethers of glycerol ethers with aliphatic $C_{12}$-$C_{18}$ alcohols, partial esters of propylenglycol with aliphatic $C_6$-$C_{22}$ carboxylic acids, partial esters of polyglycerol with aliphatic $C_6$-$C_{22}$ carboxylic acids, and mixtures of the foregoing; and c. a lipophilic phase in an amount of 0% to 70% by weight of the surfactant system, represented by diacylglyerides and/or triacylglycerides with aliphatic $C_6$-$C_{22}$ carboxylic acids;

wherein the surfactant system comprises 10% to 95% by weight of the pharmaceutical composition.

40. A pharmaceutical composition prepared by the process according to claim 39, wherein said surfactant system further comprises at least one pharmaceutically compatible auxiliary, carrier or excipient.

41. A method of treating pancreatic exocrine insufficiency in a mammal or human comprising the steps of orally administering to a subject in need thereof a pharmaceutical composition in a solid dosage form with is self-emulsifiable on contact with a hydrophilic phase and a lipophilic phase, said composition comprising:
(i) an active pharmaceutical agent which
(a) is an enzyme or an enzyme mixture with at least lipolytic activity which exerts its action in the gastrointestinal tract, and
(b) is admixed with a surfactant system to form the pharmaceutical composition wherein the pharmaceutical composition does not contain an enteric coating and does not contain any lipophilic active substances to be absorbed into the bloodstream; and
(ii) wherein the surfactant system comprises a. a surfactant in an amount of 2% to 90% by weight of the surfactant system selected from either a first group or an ionic surfactant, wherein the first group consists of: polyethylene glycol fatty acid mono-esters and/or di-esters with aliphatic $C_6$-$C_{22}$ carboxylic acids; polyethylene glycol glycerol fatty acid esters with aliphatic $C_6$-$C_{22}$ carboxylic acids; polyethylene glycol alkyl mono-ethers and/or di-ethers with aliphatic $C_{12}$-$C_{18}$ alcohols, and mixtures of the foregoing; and wherein the ionic surfactant is selected from the group consisting of: lecithin, lysolecithin, phosphatidylcholine, phosphatidylethanolamine, phosphatidylglycerol, phosphatidylserine, lysophosphatidylcholine, lysophosphatidylethanolamine, lysophosphatidylglycerol, lysophosphatidylinositol, lysophosphatidic acid, lysophosphatidylserine, and mixtures of the foregoing;

b. a co-surfactant in an amount of 5% to 60% by weight of the surfactant system, selected from a group consisting of monoacylglycerides with aliphatic $C_6$-$C_{22}$ carboxylic acids, monoethers of glycerol ethers with aliphatic $C_{12}$-$C_{18}$ alcohols, partial esters of propylenglycol with aliphatic $C_6$-$C_{22}$ carboxylic acids, partial esters of polyglycerol with aliphatic $C_6$-$C_{22}$ carboxylic acids, and mixtures of the foregoing; and c. a lipophilic phase in an amount of 0% to 70% by weight of the surfactant system, represented by diacylglyerides and/or triacylglycerides with aliphatic $C_6$-$C_{22}$ carboxylic acids;

wherein the surfactant system comprises 10% to 95% by weight of the pharmaceutical composition.

42. The pharmaceutical composition prepared by the process according to claim 39, wherein the ionic surfactant is selected from the group consisting of: lecithin, lysolecithin, phosphatidylcholine, posphatidylethanolamine, phosphatidylglycerol, phosphatidylserine, lysoposphatidylcholine, lysophosphatidylethanolamine, lysophosphatidylglycerol, lysophosphatidylinositol, lysophosphatidic acid, lysophosphatidylserine, and mixtures of the foregoing.

43. A pharmaceutical composition according to claim 27 wherein the enzymes or enzyme mixture also has proteolytic and/or amylolytic activity.

* * * * *